US006232608B1

(12) United States Patent
Giebeler et al.

(10) Patent No.: US 6,232,608 B1
(45) Date of Patent: May 15, 2001

(54) OPTIMIZATION SYSTEMS IN A SCANNING FLUOROMETER

(75) Inventors: Robert Giebeler, San Jose; Thomas J. Smith, Palo Alto; Steven McNerney, San Jose; Dean Hafeman, Hillsborough; Gillian Humphries, Los Altos, all of CA (US)

(73) Assignee: Molecular Devices Corporation, Sunnyvale, CA (US)

( * ) Notice: Subject to any disclaimer, the term of this patent is extended or adjusted under 35 U.S.C. 154(b) by 0 days.

(21) Appl. No.: 09/274,796

(22) Filed: Mar. 23, 1999

Related U.S. Application Data

(60) Provisional application No. 60/096,999, filed on Aug. 18, 1998.

(51) Int. Cl.$^7$ .................................................. G01N 21/64
(52) U.S. Cl. ..................................... 250/458.1; 250/459.1
(58) Field of Search ............................. 250/458.1, 459.1, 250/461.1, 461.2

(56) References Cited

U.S. PATENT DOCUMENTS

| | | | |
|---|---|---|---|
| 4,501,970 | * | 2/1985 | Nelson . |
| 4,626,684 | * | 12/1986 | Landa . |
| 4,942,303 | * | 7/1990 | Kolber et al. ...................... 250/458.1 |
| 5,591,981 | | 1/1997 | Heffelfinger et al. . |
| 5,784,152 | | 7/1998 | Heffelfinger et al. . |
| 5,851,488 | * | 12/1998 | Saul et al. ................................ 422/67 |

FOREIGN PATENT DOCUMENTS

WO 97/11351   3/1997   (WO) .
WO 97/11352   3/1997   (WO) .

* cited by examiner

*Primary Examiner*—Constantine Hannaher
*Assistant Examiner*—Otilia Gabor
(74) *Attorney, Agent, or Firm*—McCutchen, Doyle, Brown & Enersen, LLP; David G. Beck

(57) ABSTRACT

A method and apparatus for determining the fluorescence, luminescence, or absorption of a sample is provided. The sample may either be contained within a cuvette or within one or more sample wells within a multi-assay plate. A combination of a broadband source, monochromator, and a series of optical filters are used to tune the excitation wavelength to a predetermined value within a relatively wide wavelength band. A similar configuration is used to tune the detection wavelength. In one aspect, multiple optical filters are coupled to the excitation source subassembly, thus allowing the system to be quickly converted from one optical configuration to another. In another aspect, the excitation light and the detected sample emissions pass to and from an optical head assembly via a pair of optical fibers. In another aspect, an optical scanning head assembly is used that includes mirrored optics for coupling the excitation source to the sample and the emitted light to the detector. In another aspect, time tags are recorded for samples contained within a multi-assay plate to monitor compositional time dependent properties or to ensure the accurate comparison of individual samples.

29 Claims, 26 Drawing Sheets

OPTIMIZATION SYSTEMS IN A SCANNING FLUOROMETER

CROSS-REFERENCES TO RELATED APPLICATIONS

This application claims benefit from Provisional Application Ser. No. 60/096,999, filed Aug. 18, 1998.

FIELD OF THE INVENTION

The present invention relates generally to detection systems, and more particularly, to a method and apparatus for detecting fluorescence, luminescence, or absorption in a sample.

BACKGROUND OF THE INVENTION

In biology as well as other related scientific fields, samples are routinely characterized by examining the properties of fluorescence, luminescence, and absorption. Typically in a fluorescence study, selected tissues, chromosomes, or other structures are treated with a fluorescent probe or dye. The sample is then irradiated with light of a wavelength that causes the fluorescent material to emit light at a longer wavelength, thus allowing the treated structures to be identified and to some extent quantified. The wavelength shift between the peak excitation wavelength and the peak fluorescence wavelength is defined as the Stokes shift and is the result of the energy losses in the dye molecule.

In a luminescence study, the sample material in question is not irradiated in order to initiate light emission by the material. However, one or more reagents may have to be added to the material in order to initiate the luminescence phenomena. An instrument designed to monitor luminescence must be capable of detecting minute light emissions, preferably at a predetermined wavelength, and distinguishing these emissions from the background or ambient light.

In a typical light absorption study, a dye-containing sample is irradiated by a light source of a specific wavelength. The amount of light transmitted through the sample is measured relative to the amount of light transmitted through a reference sample without dye. In order to determine the concentration of dye in a sample, both the light absorption coefficient (at the wavelength used) and the pathlength through the sample must be known. Other relative measurements may also be of interest, for example determining the wavelength dependence of the absorption.

In general, an instrument designed to determine the fluorescence of a sample requires at least one light source emitting at one or more excitation wavelengths and a detector for monitoring the fluorescence emissions. This same instrument can often be used for both luminescence and absorption measurements with only minor changes.

U.S. Pat. No. 4,626,684 discloses a fluorescence measurement system for use with a multi-assay plate. The disclosed system uses concave holographic gratings to control both the excitation and emission detection wavelengths. Optical fibers are used to couple the optical scanning head to both the source and detector subassemblies. The paths of both the excitation light and the fluorescent emissions are orthogonal to the surface of the material under study.

U.S. Pat. No. 4,501,970 discloses a fluorometer for use with multi-assay plates. The disclosed system directs the excitation beam of light through the open top of the sample holding vessel and receives the fluorescent emission through this same opening. The system uses a series of mirrors and masks to decouple the excitation light from the emitted fluorescence, thereby reducing the noise signal level in the detector and increasing the sensitivity of fluorescence detection.

From the foregoing, it is apparent that a high sensitivity, wavelength scanning fluorometer is desired.

SUMMARY OF THE INVENTION

The present invention provides a method and apparatus for determining the fluorescence, luminescence, or light absorption of a sample. The sample may either be contained within a cuvette or within one or more sample wells of a multi-assay plate. The system is designed to accommodate a variety of different multi-assay plates in which the plate dimensions as well as the number of sample wells varies.

In one aspect of the invention, an excitation means is provided for either fluorescence or absorption measurements. The excitation means includes a broadband light source, a monochromator, and a series of optical filters. This combination of optical components allows the excitation wavelength to be tuned to a predetermined value within a relatively wide wavelength band. Depending upon the dispersion of the components, bandpass values of approximately 10 nanometers are commonly achievable. A similar optical configuration is used to detect the emissions from the sample (i.e., fluorescence or luminescence) or the amount of light absorbed by the sample. The detection means includes a photomultipler tube detector, a diffraction grating, and a series of optical filters.

In another aspect of the invention, multiple optical fibers are coupled to the excitation source, thus allowing the system to be quickly converted from one optical configuration to another. For example, the source can be used to illuminate either the top or the bottom of a sample well within a multi-assay plate or to illuminate a single cuvette cell. Similarly, multiple optical fibers are coupled to the detector. The multiple detector fibers allow the system to be easily converted from detecting fluorescence or luminescence to detecting the amount of excitation light passing through the sample (i.e., for absorption measurements). The multiple detection fibers also allow the optical configuration to be converted to match the excitation configuration, e.g., cuvette cell versus multi-assay plate.

In another aspect of the invention, the excitation light and the detected sample emissions pass to and from an optical head assembly via a pair of optical fibers. The optical head assembly is coupled to a pair of guide rails and controlled by a step motor, thus allowing the head assembly to be driven along one axis of a multi-assay plate. The multi-assay plate is mounted to a carriage assembly that is also coupled to a pair of guide rails and controlled by a step motor. The carriage assembly drives the multi-assay plate along a second axis orthogonal to the first axis.

In another aspect of the invention, the system is designed to accommodate a wide range of sample intensities automatically, such as would be expected from a group of random samples within a multi-assay plate. In order to accommodate varying intensities, a photomultiplier tube detector is used and the voltage is automatically varied in order to change its gain. The automatic voltage adjustment is performed in three steps, each providing a nominal dynamic range of three decades. Alternatively, the voltage adjustment can be performed in more than three steps employing finer gradations of dynamic range.

In another aspect of the invention for use with a multi-assay plate configuration, the system is designed to minimize the effects of temperature drop from one sample to another that are due to evaporative cooling. Specifically, the plate holding carriage moves the multi-assay plate to a sample holding area between readings. Within the sample holding area the multi-assay plate is confined by an upper or lid surface that is close to the upper surface of the multi-assay plate. The sides of the multi-assay plate may also be confined. When the multi-assay plate is within this area the relative humidity above the plate rises to more than 90 percent, thus reducing evaporative cooling. This aspect of the invention is preferably coupled to a temperature regulation and air circulation system.

In another aspect of the invention, an optical scanning head assembly is used that includes mirrored optics for coupling an excitation source to the sample and the emitted light to a detector. An ellipsoidal focussing mirror is used to magnify and focus the source light projected from an optical fiber onto the sample. A portion of the source light is reflected by a beamsplitter onto a reference detector used to monitor the output of the source. The light from the ellipsoidal mirror passes through an aperture in a second ellipsoidal mirror prior to impinging upon the sample. The light emitted by the sample within the sample well (e.g., fluorescence) is reflected by the second ellipsoidal mirror and imaged onto the entrance aperture of an optical fiber coupled to the detector subassembly. The optical axes of both mirrors are slightly offset from the sample well normal. The offset minimizes the amount of light reflected from the meniscus of the sample or the bottom surface of the sample well that enters the detection subassembly.

In another aspect of the invention, time tags are recorded for samples contained within a multi-assay plate. The time tags can be used to monitor compositional time dependent properties, for example those associated with a kinetic reaction. The time tags can also be used to insure that a comparison of individual samples within a multi-assay plate is accurate and is not biased by variations in the amount of time passing between the steps of sample preparation and sample characterization. In one mode of time tagging, a time tag is recorded for each critical preparation step and each critical characterization step for every sample of interest. In a second mode of time tagging, only a single time tag is recorded for the entire multi-assay plate for each critical step of either preparation or characterization. In this mode, however, every sample of the multi-assay plate is sequentially prepared or characterized with a set interval passing between the preparation or characterization of successive samples.

A further understanding of the nature and advantages of the present invention may be realized by reference to the remaining portions of the specification and the drawings.

DESCRIPTION OF THE SPECIFIC EMBODIMENTS

System Overview

Figure 1:
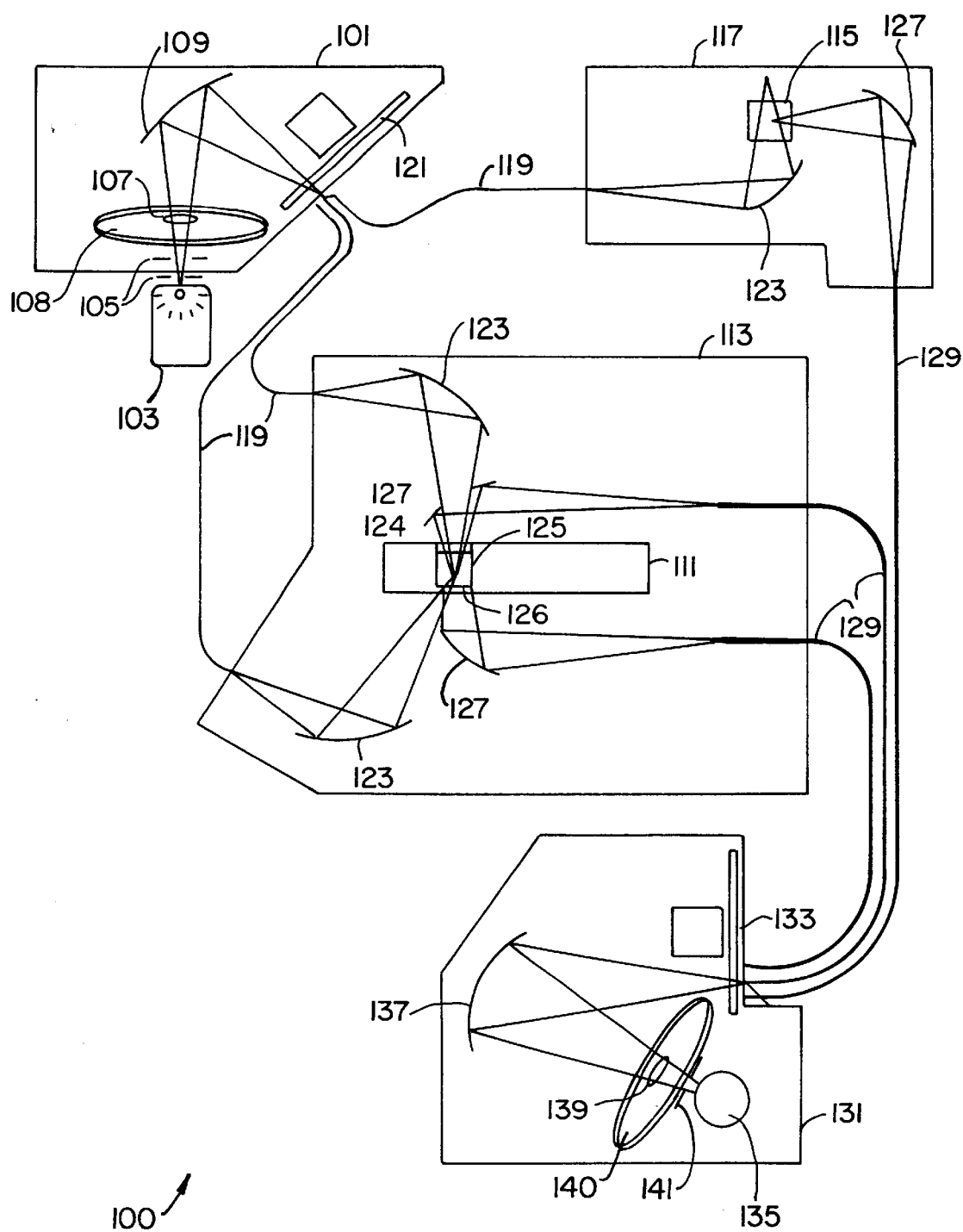
FIG. 1 schematically illustrates the detection system of the present invention.

FIG. 1 schematically illustrates the principal components of at least one embodiment of a scanning fluorometer system 100 according to the present invention. Preferably system 100 is constructed utilizing subassembly modules. This module approach offers several benefits. First, it allows a non-functioning subassembly to be easily removed and replaced with a functioning subassembly, thereby minimizing the amount of time that the system is inoperable. Second, modules can be replaced or augmented as either the user's requirements change, or as improved subassemblies become available, thus providing for system growth. Third, this approach allows for increased on-site calibration and/or maintenance.

A light source subassembly 101 within system 100 generates illumination of a predetermined wavelength. Preferably the source for subassembly 101 is a broadband source, such as a xenon flash lamp 103. The light from lamp 103 may pass through one or more apertures 105 in order to condition the light before passing through an optical filter 107 mounted in an opening of a filter wheel 108. The wavelength of light emitted by source subassembly 101 is determined by a combination of filter 107, a movable grating 109, and apertures formed by the input apertures of optical fibers 119.

The light from source subassembly 101 is used to either illuminate a well 125 of a multi-assay plate 111 contained within a multi-assay plate chamber subassembly 113 or a cuvette 115 within a cuvette chamber subassembly 117. Multi-assay plate 111 is retained by a holding fixture. The light from source subassembly 101 is transmitted to multi-assay plate chamber subassembly 113 or cuvette chamber subassembly 117 via a selected fiber of optical fibers 119. Furthermore, the source light can be transmitted either through the open top portions 124 of wells 125 or through transparent closed bottom portions 126 of wells 125, the selection of which is determined by the particular optical fiber 119 selected to couple source subassembly 101 to multi-assay plate 111. An optical shutter 121 within source subassembly 101 establishes which of fibers 119 receives light from source 103. One or more focussing mirrors 123 focus the light passing through fibers 119 into the chamber of interest, i.e., multi-assay plate well 125 or cuvette 115.

The light, either from cuvette 115, top portion 124 of well 125, or bottom portion 126 of well 125, is collected with optics 127. The collected light can be either light emitted as fluorescence or luminescence, or transmitted light used for an absorption measurement. The collected light passes through a selected optical fiber of fibers 129 to a detection subassembly 131. When transmitted light is used for an absorption measurement in wells 125, the preferred configuration is to pass the light first through top portion 124 of wells 125, then through the sample materials contained within wells 125, and finally through the bottom portion 126 of wells 125. During absorption measurements, the transmitted light is collected by optics 127 positioned under multi-assay plate 111. The collected light is then focused onto a selected fiber 129 for transmission to detector 135 in detector subassembly 131. In a first alternative configuration used for absorption measurements, as in the above configuration the light enters well 125 through top portion 124. After the light passes through the sample materials within well 125, however, it is reflected back by a mirror underneath of the sample well (not shown) and collected by optics positioned above the well (not shown). In a second alternative configuration a detector, preferably a photodiode, is located directly under the well (not shown) and collects the light transmitted through well 125 and the sample materials contained therein. In a third alternative configuration (not shown) the light enters well 125 through bottom portion 126, passes through the sample materials, passes through top portion 124, and is then collected and focussed onto a detector. In this configuration the detector may either be mounted remotely or be mounted in close proximity to top portion 124.

A shutter 133 determines which fiber 129 is monitored by subassembly 131. The light from a selected fiber 129 is focussed onto a detector 135 by a movable, focussing grating 137. Preferably detector 135 is a photomultiplier tube (i.e., PMT). The light may pass through one or more apertures 141 to reduce stray light before impinging on detector 135. The combination of grating 137, aperture 141, and a filter 139 mounted in an opening of a filter wheel 140 determines the wavelength of light detected by detector 135.

Grating 109 allows the excitation wavelength to be continuously varied over a relatively wide wavelength band. Similarly, grating 137 allows the detection wavelength to be continuously varied over a wide range of wavelengths. In the preferred embodiment of the invention, gratings 109 and 137 each have a focal length of approximately 100 millimeters, thus allowing excitation subassembly 101 and detection subassembly 131 to be relatively compact. As the gratings are preferably holographic gratings with 1200 grooves per millimeter, the dispersion of the gratings with this focal length provides a nominal 10 nanometer bandpass. In a preferred embodiment of the invention, the blaze angle of the gratings is 500 nanometers. However, the gratings may be blazed at different angles, thus further enhancing the decoupling of the excitation and fluorescence wavelengths. Preferably the arc of lamp source 103 is focused onto the entrance aperture of fiber 119.

Figure 2:
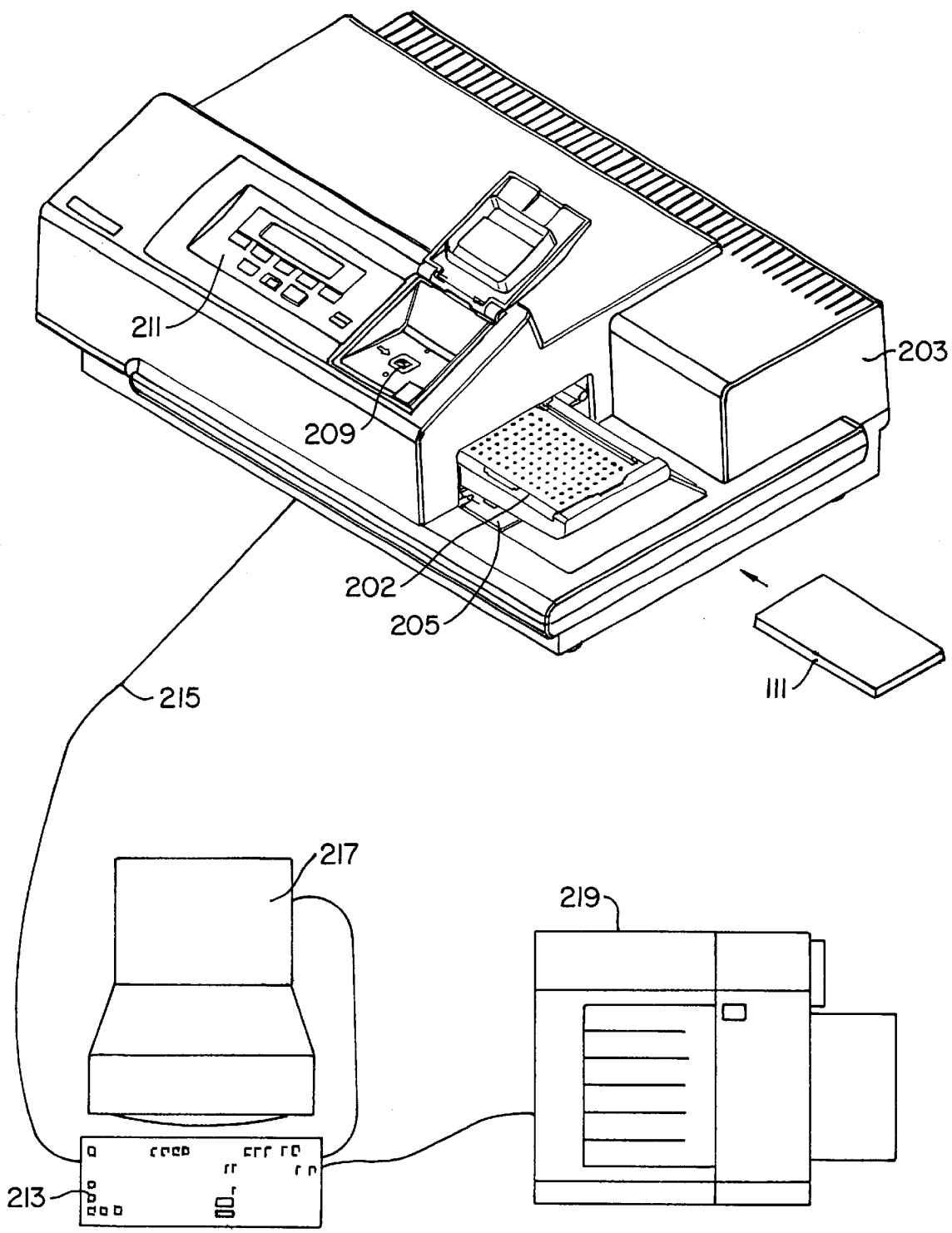
FIG. 2 is an illustration of the outer casing of one embodiment of the invention.

FIG. 2 illustrates the outer casing of one embodiment of the invention. In this embodiment a multi-assay plate 111 that is ready for testing is placed within reading chamber 202 of instrument 203 via a housing door 205. In at least one embodiment of the invention, the instrument can also be used to test a cuvette, preferably by inserting the cuvette into a cuvette port 209. A control panel 211 provides a user interface, allowing the user to initiate testing as well as set various testing protocols. Preferably control panel 211 also includes a simple readout system such as a LCD readout, thus providing the user with positive indications of selections as well as status.

Instrument 203 is preferably coupled to a data processing system 213 via a cable 215. Data processing system 213 is used to manipulate the data, store the data, and present the data to the user via either a monitor 217 or a printer 219. Depending upon the system configuration, processing system 213 can also be used to control the test itself (i.e., test initiation, test protocol settings, etc.). In the preferred embodiment, an internal processor controls at least the basic test parameters by controlling movable gratings 109 and 137, filter wheels 108 and 140, shutters 121 and 133, and the relative movement of multi-assay plate 111 to excitation optics 123 and detection optics 127.

Figure 3:
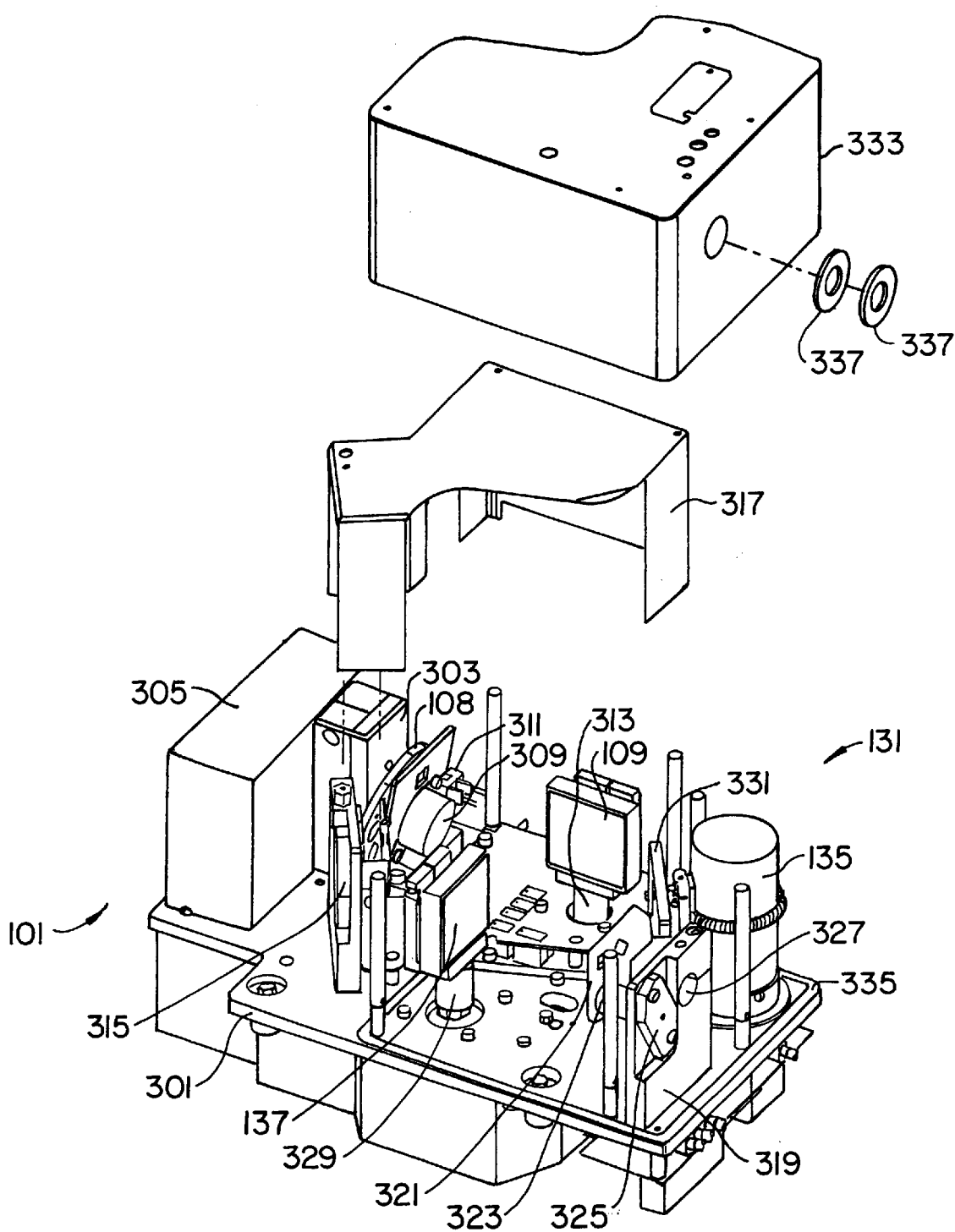
FIG. 3 is an illustration of the combined optical subassemblies.

FIG. 3 is an illustration of the optical subassemblies of the preferred embodiment of the invention. In order to decrease the overall size of system 100, in this embodiment of the invention both source subassembly 101 and detection subassembly 131 are contained on a single optical bench 301.

Source 103 is mounted within a bracket 303 and coupled to a source high voltage power supply 305. Preferably source 103 is a xenon flash lamp due to its relatively wide emittance wavelength band, ranging from the ultraviolet to the infrared. In alternative embodiments, source 103 can be a mercury arc lamp, a laser, an incandescent lamp (e.g., a tungsten lamp), or other source. The light from source 103 passes through a filter wheel 108 containing a plurality of optical filters 107. Filters 107 can be bandpass filters (i.e., pass a band of wavelengths), cutoff filters (i.e., only pass wavelengths above or below a predetermined wavelength), or any other type of optical filter that can be used to control the wavelength of light passing through the filter and impinging on optical grating 109. The position of filter wheel 108, and therefore the selected filter in the excitation beam path, is controlled by motor 309. A position sensor 311 (e.g., an optical switch) or other means is used to determine the position of wheel 108, and thus the filter 107 within the beam path. Preferably motor 309 and position sensor 311 are coupled to a controller internal to the instrument.

The light passing through the selected filter 107 in filter wheel 108 is reflected off of grating 109. Grating 109 is coupled via a shaft 313 to a fine control motor, such as a stepper motor, that is used to set the angle of grating 109 with respect to the incident light beam. Grating 109 focuses the light onto a shutter assembly 315. Covering excitation source assembly 101 is a cover 317, thus helping to minimize source light inadvertently entering the system.

Figure 4:
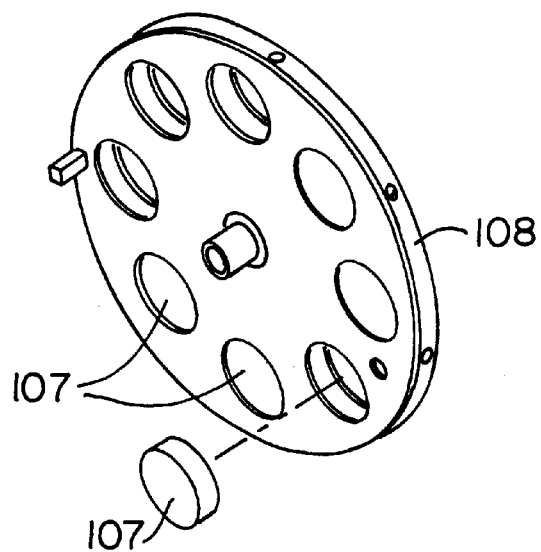
FIG. 4 is a respective view of an excitation filter wheel.
Figure 5:
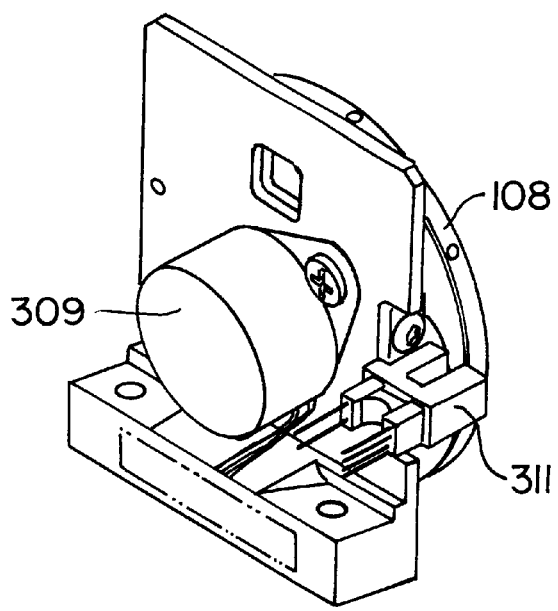
FIG. 5 is a perspective view of an excitation filter wheel assembly.

FIG. 4 is a perspective view of filter wheel 108 and filters 107 and FIG. 5 is a perspective view of the filter wheel assembly including wheel 108, motor 309, and position sensor 311. In the preferred embodiment of the invention, filter wheel 108 contains 5 longpass filters covering the wavelength bands shown in Table 1 below. Excitation filters 107 serve a dual purpose. First, the filters are used to block the second order, thereby reducing stray light. Second, a higher number of filters are used than is common so that the cutoff may be placed as close as possible to the selected wavelength, thus blocking higher orders and helping to reduce stray UV light from exciting background fluorescence in the sample. Preferably the cutoff wavelength (i.e., the wavelength of 50% nominal transmission of the longpass filters) is approximately 10 nanometers below the selected wavelength. Light wavelengths less than the cutoff wavelength are substantially blocked while longer wavelengths are substantially transmitted to excitation grating 109.

TABLE 1

| Cutoff Selection Filter No. | λ (nm) | Endpoint and Kinetic Modes Excitation λ (nm) |
| --- | --- | --- |
| 1 | No Filter | 200–330 |
| 2 | 320 | 330–410 |
| 3 | 395 | 410–510 |
| 4 | 495 | 510–610 |
| 5 | 590 | 610–710 |
| 6 | 695 | 710–800 |

Figure 6:
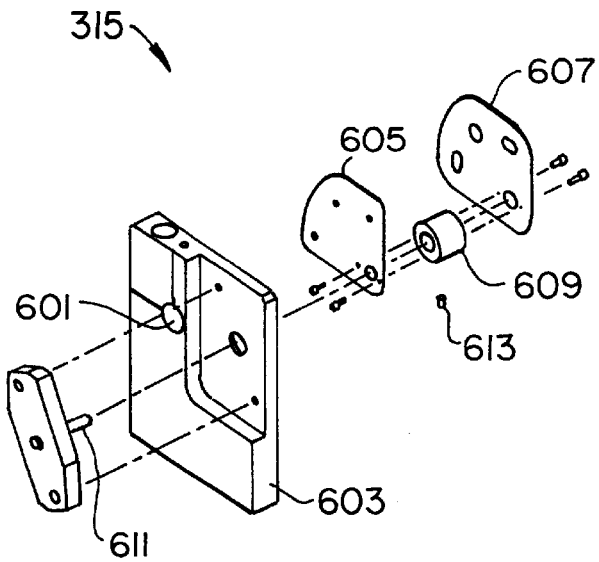
FIG. 6 is an exploded view of a shutter assembly.

An exploded view of shutter assembly 315 is shown in FIG. 6. Shutter assembly 315 is used to control the coupling of the light beam focussed by grating 109 onto one or more optical fibers. In the preferred embodiment, a single fiber is mounted within a fiber mounting opening 601 in a bracket 603.

In an alternate embodiment, multiple fibers are mounted within bracket 603, shutter assembly 315 controlling which, if any, of the fibers receive light from grating 109. In the alternate embodiment, shutter assembly 315 includes an inner shutter plate 605 and an outer shutter plate 607. Shutter plates 605 and 607 are coupled via a bushing 609 to a mounting hub bracket 611. As illustrated, shutter plates 605 and 607 are placed into the desired location and locked onto hub bracket 611 via a set screw 613. Alternatively, hub bracket 611 may be replaced with a motor, the motor allowing the position of the shutter plates to be remotely controlled.

Figure 7:
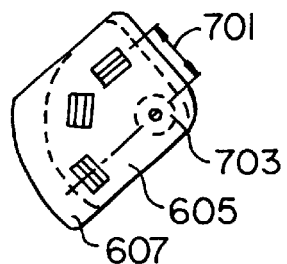
FIG. 7 is an illustration of the combined shutter plates utilized in the shutter assembly shown in FIG. 6.

FIG. 7 is an illustration of combined shutter plates 605 and 607 showing the alignment of the apertures of the two plates. As shown, the distance 701 between each set of aligned apertures and the center of rotation 703 varies. Therefore as the combined shutter plates are rotated along axis 703, the position of the light beam passing through the shutter assembly changes. Given the shutter assembly illustrated in FIGS. 6 and 7, three fibers could be co-located within bracket 603, combined shutter plates 605 and 607 determining which of the fibers receive light from the excitation source. As illustrated, shutter plates 605 and 607 have three apertures thereby limiting the total number of fibers that can be coupled to the excitation source through this assembly to three. However, the number of apertures and thus the number of fibers are primarily limited by the size of the light beam focussed by grating 109 onto the shutter assembly. Furthermore, by varying the aperture sizes of shutter plates 605 and 607, the size of the passed beam can also be controlled.

The light from multi-assay plate chamber subassembly 113 or cuvette chamber subassembly 117 enters detection subassembly 131 via a shutter assembly 319. The design of shutter assembly 319 is substantially the same as shutter assembly 315 and includes a pair of shutter plates 321, a bushing 323, and a hub bracket 325. Although in the illustrated embodiment there is only a single fiber opening 327, bracket 325 could include multiple fiber openings thereby allowing shutter plates 321 to control which fiber passes light through to the detector. Additionally and as described above, shutter plates 321 can also be used to control the size of the beam simply by varying the size of the apertures.

Figure 8:
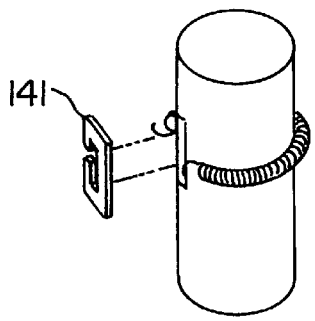
FIG. 8 is an illustration of a PMT housing and slit.

Light passing through shutter plates 321 is focussed by grating 137 onto detector 135. Grating 137 is coupled to a high accuracy motor via a coupler 329. The combination of rotatable grating 137 and a filter assembly 331 determines the detected light wavelength. Due to the location of filter assembly 331 between grating 137 and detector 135, native fluorescence in filter 139 is substantially eliminated. The entire detection subassembly is enclosed with a cover 333 that is attached to optical bench plate 301. A gasket 335 insures a light seal between cover 333 and plate 301. Similarly gaskets 337 insure a light seal between cover 333 and optical fiber 129 coupled to shutter assembly 319 via opening 327. Cover 333 as well as the various gaskets (e.g., 335 and 337) substantially reduce the amount of stray light entering detector 135. As illustrated in FIG. 8, attached to the cover of detector 135 is slit aperture 141 that also enhances the rejection of stray light in the present invention.

Figure 9:
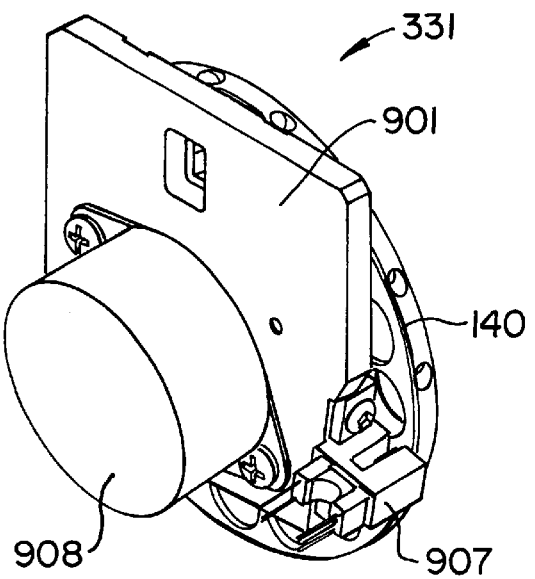
FIG. 9 is a perspective view of an emission filter wheel assembly.
Figure 10:
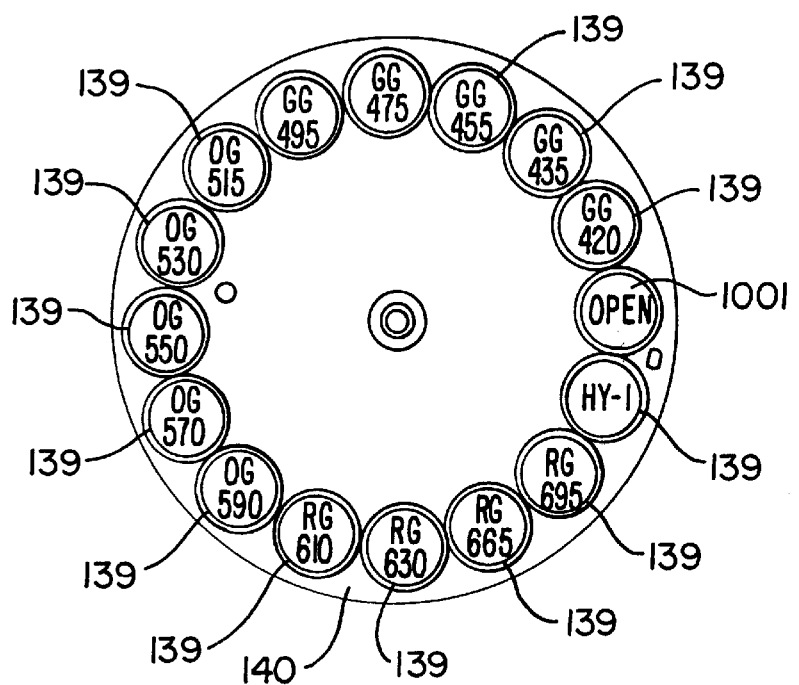
FIG. 10 is an illustration of an emission filter wheel, including filters.

Filter assembly 331 is shown in greater detail in FIGS. 9 and 10. As shown in FIG. 9, emission filter assembly 331 includes a bracket 901, a filter wheel 140, a stepper motor 905, and a filter wheel position sensor 907 such as an optical sensor. Motor 905 is used in conjunction with position sensor 907 and either an internal or external processor to place the appropriate filter 139 in the optical beam path. As illustrated in FIG. 10, filter wheel 140 includes 15 filters 139 as well as an open filter space 1001. In different embodiments filter wheel 140 may include fewer or greater numbers of filters. Filters 139 can be bandpass filters, cutoff filters, or any other type of optical filter that can be used to control the wavelength of light impinging on detector 135. In the preferred embodiment of the invention filters 139 are long pass cutoff filters.

As previously noted, the present invention can be used to measure fluorescence, luminescence, or absorption. In the fluorescence mode, the principal limiting factor in achieving high sensitivity is the background. A major contributor to the background is stray light from the excitation source. A portion of this stray light is due to the close proximity of the excitation and fluorescence emission wavelengths and the difficulty associated with preventing the excitation source wavelengths from passing through the optical assembly and into the detector. Another portion of the stray light is due to light that follows a non-direct, non-intentional path into the detector, e.g., reflections off of mounting brackets. The present invention limits the latter type of stray light by enclosing both the excitation and detection subassemblies 101 and 131, respectively, and using optical fibers to couple the various optical assemblies.

In a typical fluorometer, the band of wavelengths used to excite the fluorescent material is separated from the band of wavelengths passed to the detector by using monochrometers having prisms, or gratings, for wavelength dispersion and an exit slit to select the wavelength of interest or by using optical filters. Unfortunately neither a grating nor an optical filter is capable of absolutely eliminating the passage of undesired wavelengths. In addition, since the intensity of the excitation source is typically at least six orders of magnitude greater than the intensity of the fluorescent emissions, neither gratings nor optical filters alone can provide the desired sensitivity since some small fraction of in-band source light still reaches the detector. The present invention uses optical filters 107 and 139 in conjunction with both an excitation and an emission monochrometer having, respectively, gratings 109 and 137. The combination of filters and gratings further decreases the amount of source light outside of the excitation wavelength band, and thus within the emission wavelength band, reaching the detector. As a result, the present invention is capable of extremely high detection sensitivities.

In order to achieve high sensitivity the present invention also utilizes both apertures and absorbing beam blockers. For example, shutters 321 substantially limit the light reaching grating 137 to light exiting a selected one of optical fibers 129. In addition, slit 141 limits the viewing angle of detector 135 to grating 137. Similarly, apertures and beam blockers are used in excitation subassembly 101 to limit the light illuminating grating 109 as well as to limit the viewing angle of the exit aperture (formed by each entrance slit of optical fibers 119).

Although the combination of optical filters and gratings is capable of achieving improved sensitivity through the reduction in stray light, this combination may also reduce the level of light in the desired wavelength band to an unacceptable level. In order to avoid this problem, the invention preferably uses at least 15 different long wavelength pass emission filters 139. By using a large number of filters, the difference in cutoff wavelength for adjacent filters is small in comparison to the typical minimum Stokes shift. For example, assuming a desired wavelength band of approximately 400 to 700 nanometers, 16 filters with a nominal 20 nanometer spacing in cutoff wavelength can be used.

Due to the combination of optical filters and gratings in the present invention, the system is preferably capable of operating in several different modes, thus insuring that the best performance for a particular sample is achieved. Specifically, the user is able to set the system to operate either in a manual mode or in an automated mode. In the latter mode the user can select the system to provide either excitation priority or emission priority.

Preferably automated emission priority mode is the default setting except when the user is operating in the emission scan mode. In the automated emission priority mode the system compares the selected emission wavelength of emission grating 137 to the 50 percent transmission point for each of the emission filters 139. The system then selects a longpass filter offering a cutoff wavelength (e.g., 50 percent maximal transmission wavelength) as shown in Table 2 below. Table 2 consists of all of the possible emission wavelengths selectable by emission grating 137 and the corresponding filters (as indicated by their cutoff wavelengths) which are selected automatically. For example, if a user selects an emission wavelength of 500 nanometers, the system would review the look-up table which indicates that the cutoff wavelength for the selected filter is 495 nanameters. At emission wavelengths below 415 nanometers, no emission filter is selected.

TABLE 2

| Automatic Cutoff Selection | | Endpoint and Kinetic Modes |
|---|---|---|
| Filter No. | λ (nm) | Emission λ (nm) |
| 1 | None | <415 |
| 2 | 420 | 415–434 |
| 3 | 435 | 435–454 |
| 4 | 455 | 455–474 |
| 5 | 475 | 475–494 |
| 6 | 495 | 495–514 |
| 7 | 515 | 515–529 |
| 8 | 530 | 530–549 |
| 9 | 550 | 550–569 |
| 10 | 570 | 570–589 |
| 11 | 590 | 590–609 |
| 12 | 610 | 610–629 |
| 13 | 630 | 630–664 |
| 14 | 665 | 665–694 |
| 15 | 695 | 695–900 |

As noted above, in the preferred embodiment of the invention the emission priority mode is the default as it provides the best performance for most assays. The exception to this default is in emission scanning. In emission scanning mode no emission filters 139 are automatically utilized because this would mean filter changes during scanning, resulting in unwanted discontinuities. Cutoff filters (a single choice per emission scan) may be added manually for optimization purposes. In excitation scanning mode, emission filters 139 are automatically selected according to Table 2.

In the alternative excitation priority mode, the system compares the selected excitation wavelength to the cutoff wavelength for each of the emission filters 139. The system then selects the filter offering a cutoff wavelength that is both nearest to and greater than (in wavelength) the selected excitation wavelength. For example, if a user selects an excitation wavelength of 400 nanometers, and assuming the filter performance disclosed in the previous example, the system would select the 420 nanometer cutoff filter. This filter has a 50 percent maximal transmission wavelength at 420 nanometers and greater transmission at longer wavelengths.

Scanning Assembly

FIGS. 11–15 illustrate various aspects of the sample scanning assembly of the invention. Although in at least one embodiment of the invention the system is used to read a cuvette using cuvette port 209, the primary application for this invention is reading multi-assay plates. Furthermore the preferred embodiment of the invention is designed to be adaptable to multi-assay plates of varying configurations (i.e., varying quantities and sizes of sample wells, various plate sizes, etc.).

Figure 11:
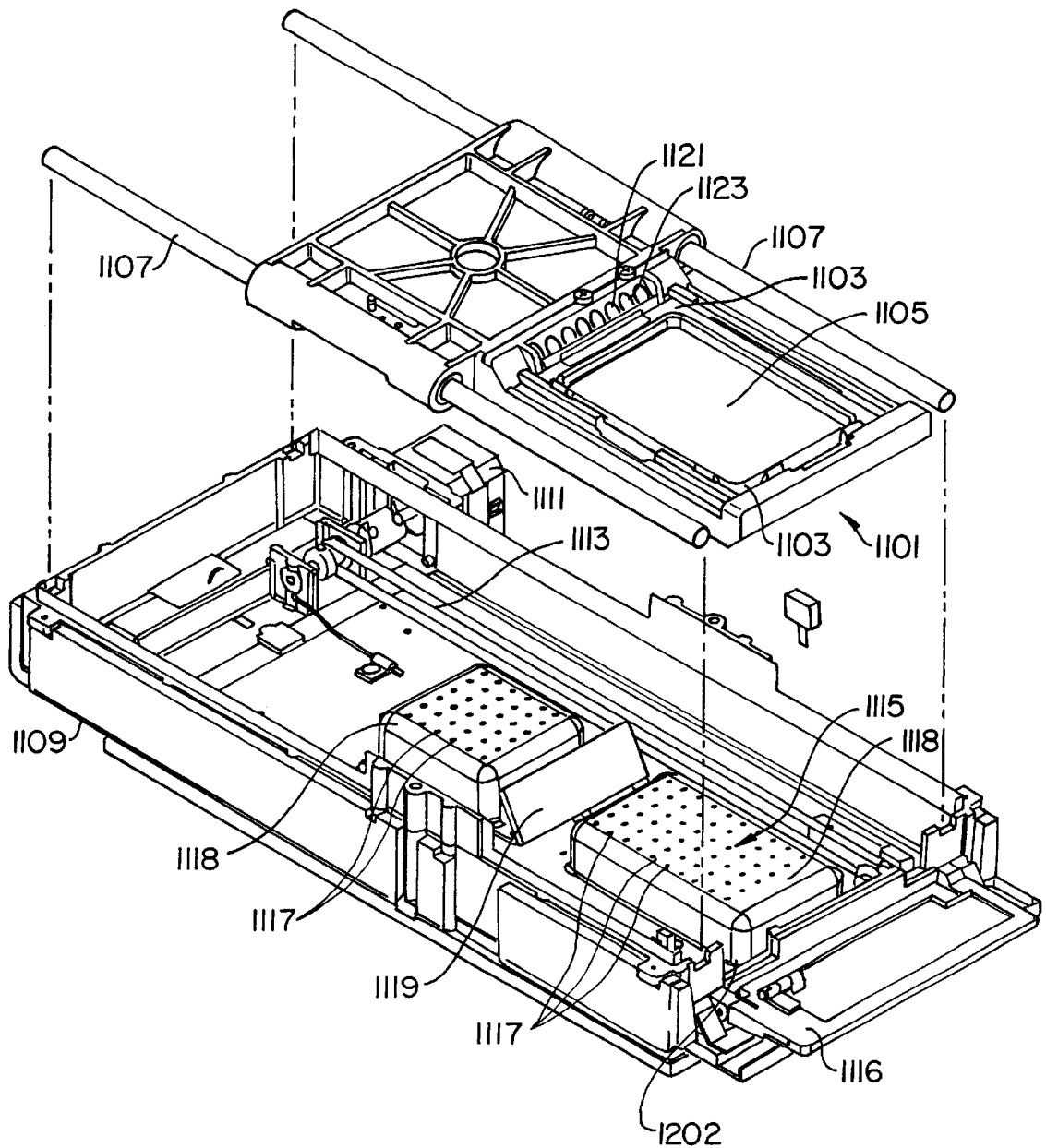
FIG. 11 is an illustration of a multi-assay plate carriage assembly according to the invention.

In FIG. 11, a sample plate holding fixture 1101 is designed to accommodate multi-assay plates of standard dimensions (e.g., 86 by 129 millimeters). In order to accommodate other sized plates, an adaptor plate (not shown) is mounted within fixture 1101, the non-standard plate fitting within the adaptor plate. Fixture 1101 supports the multi-assay plate or adaptor plate along the edges using a support frame 1103. Thus an area 1105 immediately under the sample wells of the multi-assay plate remains open, allowing a variety of sample measurements to be made that require access to both the upper and lower surfaces of the sample wells. Holding fixture 1101 slides along a pair of railings 1107 that are mounted to a base assembly 1109. A drive motor 1111 moves fixture 1101 and thus the multi-assay plate along a first axis parallel to railings 1107 by using a belt and pulley system 1113.

Figure 12:
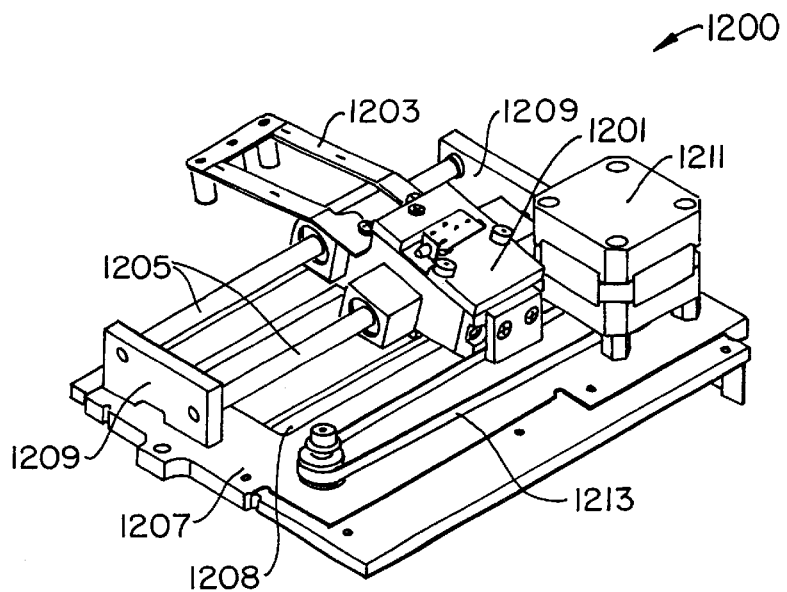
FIG. 12 is an illustration of a scanning optical stage assembly according to the invention.

FIG. 12 is an illustration of the optical scanning assembly 1200. Scanning assembly 1200 allows an optical head 1201 to be scanned along a second axis perpendicular to railings 1107. Thus scanning assembly 1200, used in conjunction with canning fixture 1101, allows an optical head 1201 to be scanned in two dimensions, thereby providing a means of analyzing each well of a two-dimensional array of wells within a multi-assay plate.

Figure 13:
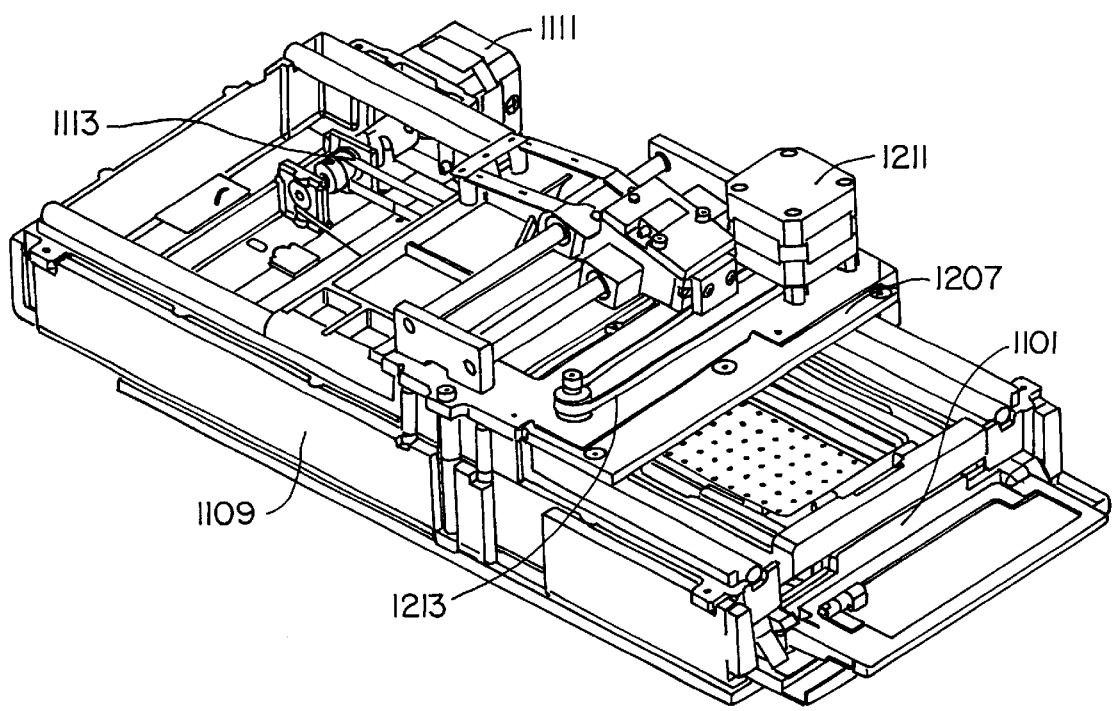
FIG. 13 is an illustration of the combined carriage and optical stage assemblies.
Figure 14:
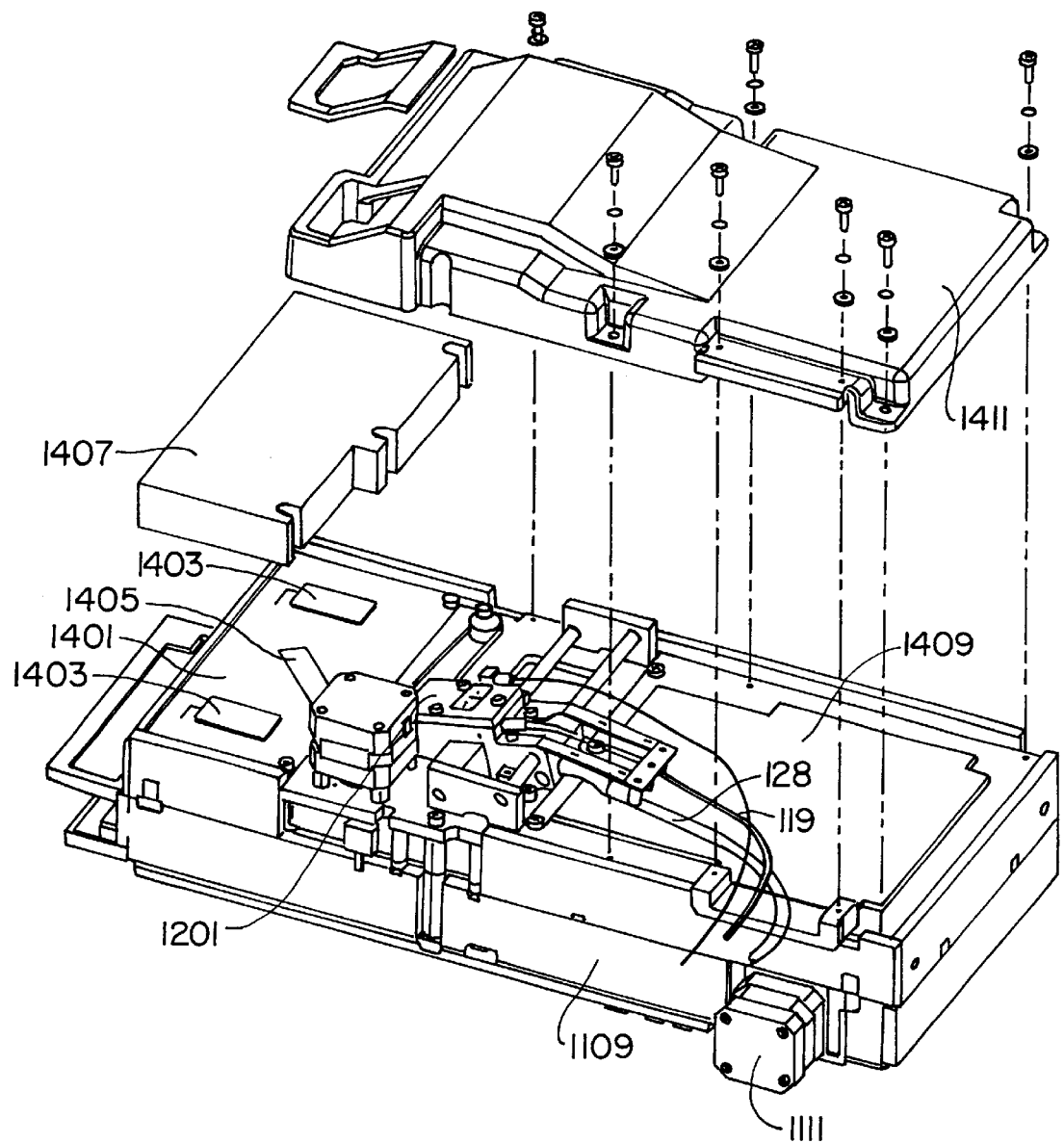
FIG. 14 is an illustration of a portion of the temperature control system used with the present invention.

In the preferred embodiment of the invention, optical head 1201 includes the optics required to illuminate the sample as well as the optics necessary to gather the emitted light. Optical fibers 119 and 129, although not shown in this illustration, are coupled to optical head 1201 via a strain relief bracket 1203. Optical head 1201 slides along a pair of railings 1205 that are mounted to a bottom assembly plate 1207 via a pair of brackets 1209. A drive motor 1211 and a belt and pulley system 1213 move optical head 1201 along a second axis orthogonal to the first axis. FIG. 13 is an illustration of optical scanning assembly 1200 mounted to base assembly 1109. Underlying multi-assay plate holding fixture 1101 is also shown in this figure.

In the preferred embodiment of the invention, scanning motors 1111 and 1211 are both under the control of an internal processor. Typically prior to use, the user inputs the sample plate configuration (e.g., how many wells, plate type, well size, etc.). The user then programs the internal processor to scan the designated sample plate utilizing one of a variety of scan modes. For example, an on-the-fly scanning mode can be used in order to minimize the amount of time it takes to read a sample plate by eliminating the acceleration and deceleration times. In this mode fixture 1101 and optical scanning head 1201 are scanned in a continuous fashion, for example utilizing a zig-zag pattern. Source 103 is flashed as optical head assembly 1201 passes over each well, thus allowing a single measurement to be made for each well. Alternatively, processor 1101 can be programmed to place optical head 1201 over each well for a predetermined period of time, allowing a predetermined number of sample readings (initiated by flashes emitted by source 103) to be made for each well.

Many fluorescence, luminescence, and absorption measurements are extremely sensitive to outside environmental factors such as temperature. This effect can become an even greater problem as the number of sample wells per multi-assay plate increase, leading to variations across the plate.

One approach to overcoming the environmental problem is to simply control the temperature of the reading chamber. This approach, however, may do little to minimize the effects of temperature drop caused by evaporative cooling. A second approach is to combine temperature control with the use of a multi-assay plate cover. Although the cover minimizes evaporative cooling and allows for temperature control, it also typically leads to a degradation in instrument sensitivity due to the effects of the lid on the optical system (i.e., increased stray light due to cover scatter, absorption by the lid, etc.).

The present invention overcomes these problems through the use of a virtual lid in combination with a temperature control system. In the preferred embodiment, carriage 1101 moves multi-assay plate 111 to an area 1115 between system readings. A lid 1401 is directly above this area. Additional members, for example made of foam, can also be used to further enclose the multi-assay plate when it is in area 1115. The bottom plate 1207 of optical head 1201 rests on the top side of lid 1401 (i.e., opposite to reading chamber 202). An opening 1208 exists in both bottom plate 1207 and lid 1401, thus allowing excitation and emission light to pass from the optical head to the samples contained in the multi-assay plates within chamber 202. Preferably the dimensions of opening 1208 are about 1.2 millimeters by 104 millimeters. When carriage 1101 moves multi-assay plate 111 below lid 1401, the lid surface is approximately 10 millimeters above the surface of the multi-assay plate and the sides of the multi-assay plate are tightly confined. As such, once the multi-assay plate is moved into resting position 1115 and the access door 1116 has been closed, the humidity above the plate rises to more than 90 percent, thus reducing evaporative cooling. This system reduces the variations from sample well to sample well within a multi-assay plate to preferably less than $\pm 0.2°$ C., and generally to less than $\pm 0.5°$ C.

In the illustrated embodiment, variations in multi-assay plate size are accommodated by using various adaptor plates. The adaptor plates not only insure that the multi-assay plate fits support frame 1103, they can also be used to insure that the top of the multi-assay plate is sufficiently close to the surface of lid 1401 to minimize temperature variations between the wells. In an alternate embodiment, the relative distance between lid 1401 and the top of a multi-assay plate in carriage assembly 1101 can be optimized by adjusting either the vertical position of the lid or the carriage assembly carrying multi-assay plate 111. In this embodiment either the lid or the carriage assembly is coupled to a motor, the motor under the control of the internal processor. Preferably a sensor (e.g., optical sensor, mechanical position sensor, etc.) is used in conjunction with this motor and processor 1101 to control the separation between the multi-assay plate and lid 1401. Alternatively, the user can input the type of multi-assay plate in use and the internal processor can use a look-up table to determine the amount of adjustment necessary for the type of multi-assay plate in use.

In order to control the temperature of area 1115 as well as the rest of reading chamber 202, one or more heaters 1403 are attached to various portions of the reading chamber. Preferably heaters 1403 are attached to lid 1401 as shown. One or more temperature monitors (e.g., thermistors) 1405 are used to monitor the temperature of the reading chamber. An outer cover 1407 is coupled to lid 1401 to facilitate temperature control within this area. Other covers such as an internal cover 1409 and an outer cover 1411 enclose the remaining upper portion of the reading chamber, thus further aiding in controlling the temperature of the system.

Figure 15:
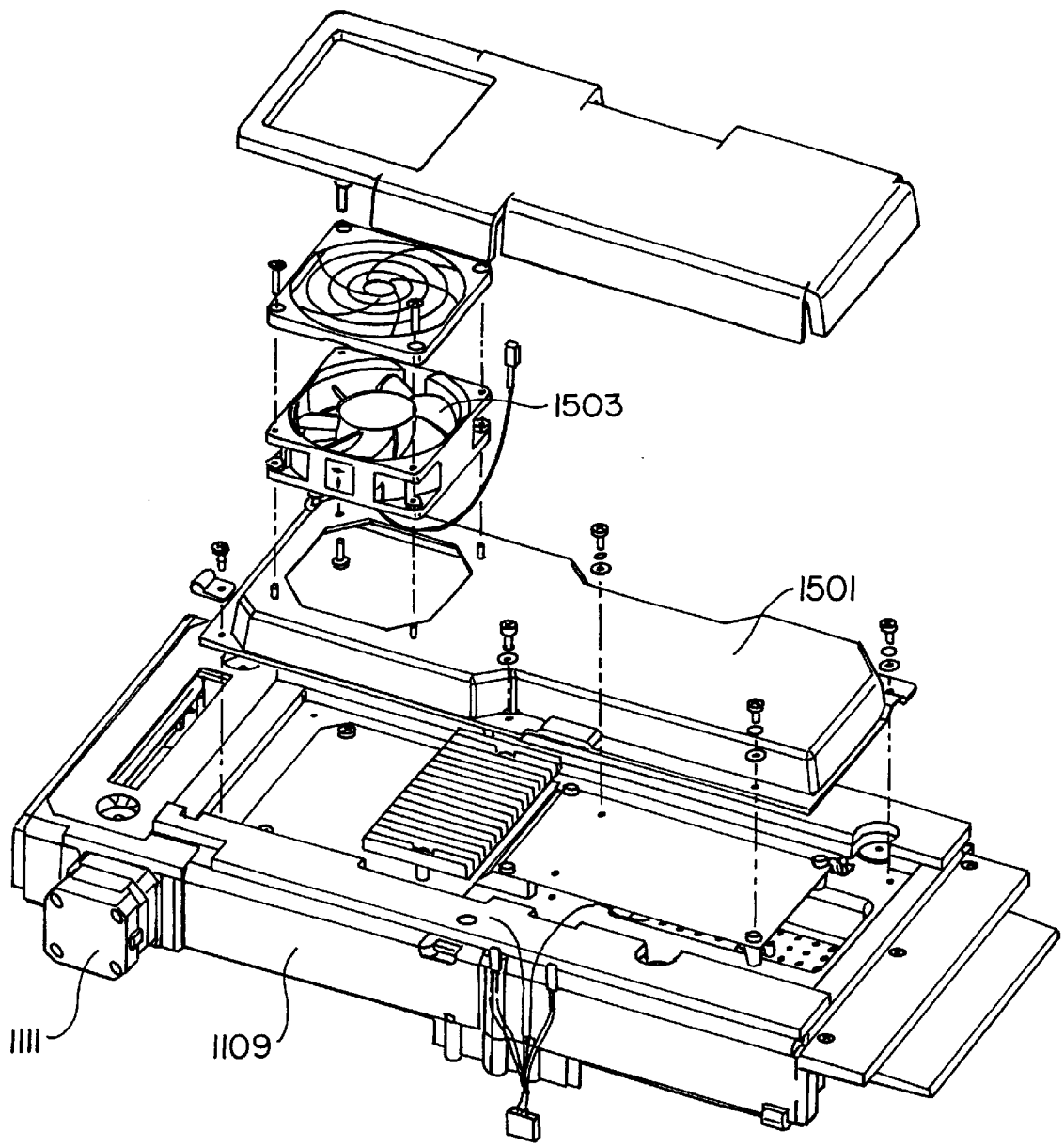
FIG. 15 is an illustration of the underside of the base assembly of the preferred embodiment of the invention.

FIG. 15 is an exploded view of the underside of base assembly 1109. Attached to base assembly 1109 is an air circulation enclosure 1501. A fan 1503 forces air through enclosure 1501. The air passes through perforations 1117 within the raised portions 1118 of base structure 1109 as shown in FIG. 11. The air circulation system, including perforations 1117, insure temperature uniformity throughout the reading chamber without causing undue air movement above the multi-assay plate.

Detection System

The present invention can be used in a variety of different modes, including end-point, kinetic, spectrum, and excitation or emission wavelength scanning. Furthermore, the system can be used with either multi-assay plates or single cuvettes. One of the many advantages of the present invention is the ability to scan either or both the excitation wavelength and the detected wavelength using gratings 109 and 137 as well as filters 107 and 139. This capability allows a user to determine accurately not only the intensity of a detected emission, but also its source (e.g., expected fluorophore, spectral convolution due to multiple fluorophores, background, etc.). Furthermore, the tunability of the excitation and emission wavelengths allow both the excitation wavelength and the detected emission wavelengths to be optimized while minimizing background detection, thereby achieving optimal instrument performance.

The principal difficulty in measuring fluorescence in a multi-sample format such as a multi-assay plate is the range of sample intensities typically encountered, often covering six orders of magnitude. In addition, if the detector is not optimized for each reading, it may either be saturated or operating below its peak sensitivity. Lastly, the fluorescence of each sample of the entire multi-assay plate must be quickly determined or the instrument is of limited use.

The present invention solves the above problems by using a photomultiplier tube (i.e., PMT) as detector 135 and, in at least one embodiment, automatically varying the voltage of the PMT detector in order to change its gain. Preferably the automatic voltage adjustment is performed in three steps, each providing a nominal dynamic range of three decades. Each time the voltage is changed there is a delay, typically between 0.1 and 10 milliseconds, to provide sufficient time for detector stabilization. If the samples loaded into the multi-assay plate are highly random and exhibit large variations in molar concentration, the system will have to undergo many voltage changes thus increasing the plate reading time. This effect is most severe when the instrument is operating in the on-the-fly scanning mode in which each sample well is irradiated with a single flash of source light, typically on the order of a 3 microsecond flash. In this mode, depending upon the system configuration, if a voltage change is necessary either the individual well or the entire column must be re-read.

In the preferred embodiment of the invention the user is able to select either an automatic mode of operation or a manual mode of operation. In the manual modes of operation the PMT detector voltage is set manually, thus avoiding the time delays that can be encountered when the system automatically controls the detector voltage. In one manual mode, the user sets the detector voltage low enough to avoid detector saturation during any reading. Unfortunately this voltage setting may sacrifice detector sensitivity. In another manual mode, the user sets the detector voltage high enough to maximize sensitivity. In this case readings from sample wells containing high concentrations of analyte will be saturated and therefore invalid. Therefore the capability of selecting from the different modes of operation allows the user to select the highest priority characteristic; wide dynamic range, minimal measurement time, or saturation avoidance. The various modes of operation are described in further detail in a later section of the specification.

Figure 16:
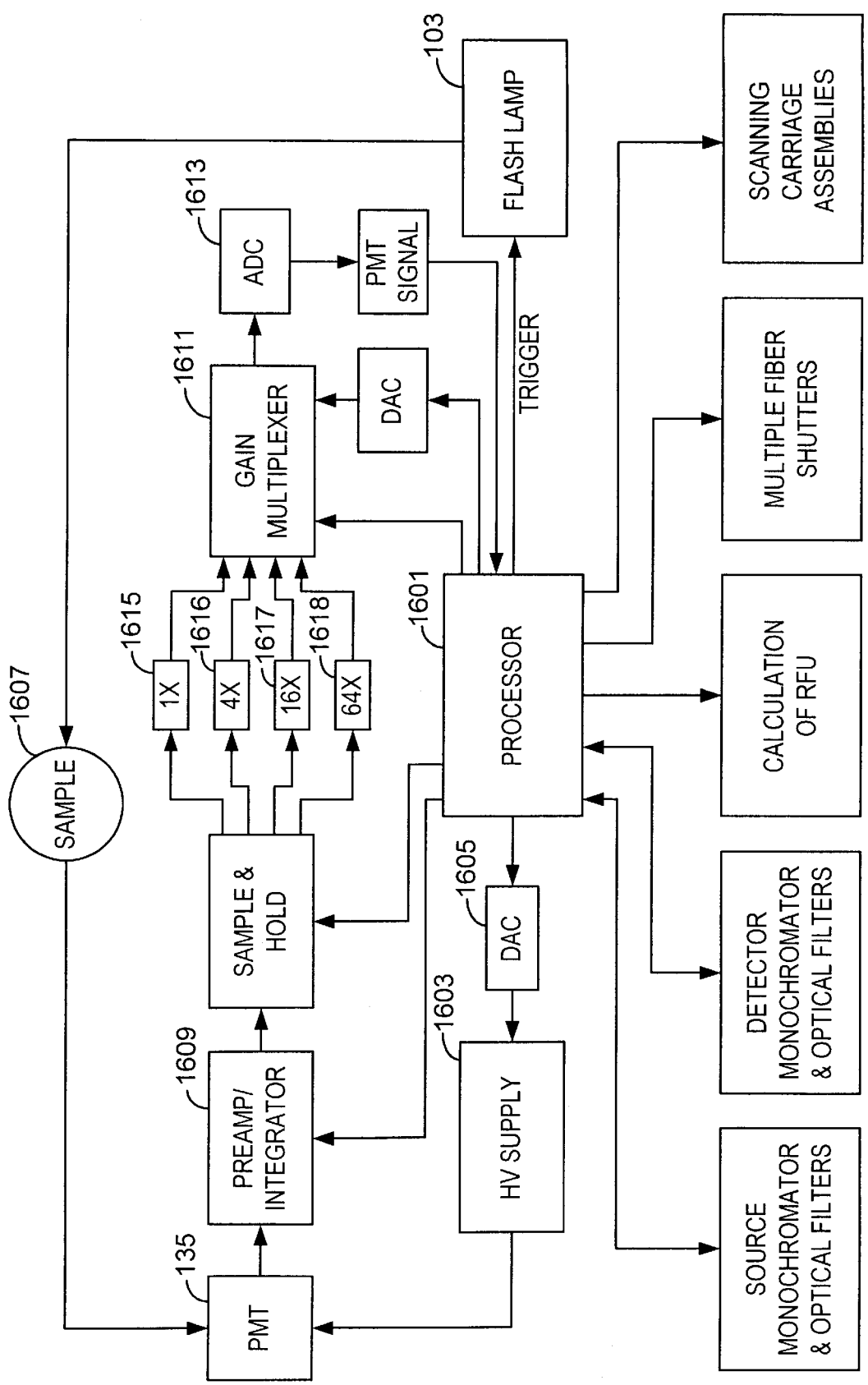
FIG. 16 is a block diagram of the detection scheme in the preferred embodiment of the invention.

FIG. 16 is a block diagram of the preferred embodiment of the detection circuit. In this system an internal processor 1601, preferably internal to instrument 100, controls the various aspects of the system as well as calculating the fluorescence for each sample. It is understood that processor 1601 may, in fact, utilize several processors to perform the various functions of the invention. Processor 1601 controls the gain of PMT detector 135 by controlling the output of the PMT high voltage power supply 1603 via a digital to analog converter 1605. In the preferred embodiment of the invention, processor 1601 receives information from sensor 311 and controls filter wheel 108 via motor 309 and similarly receives input from sensor 807 and controls filter wheel 140 via motor 905. In addition, processor 1601 sends signals to the motors controlling the rotation of gratings 109 and 137 in order to control the wavelength of the excitation and emission monochromators. If shutter slits 605/607 and 321 are coupled to stepper motors, these motors can also be controlled by processor 1601. Preferably processor 1601 also controls the motion of the sample plate scanning motors.

Processor 1601 controls the output of source 103 by controlling when the source is triggered. As illustrated in the FIG. 16 block diagram, the output of source 103 irradiates a sample 1607, the emitted fluorescence from sample 1607 being detected by detector 135. The current signal generated by PMT detector 135 is integrated by an op-amp/integrating capacitor 1609. The charge level (i.e., voltage) is measured before and after each flash of source 103 and the difference (i.e., PMT signal) is calculated. The output signal from op-amp/integrating capacitor 1609 passes to multiple gain amplifiers 1615–1618. Although the preferred gain amplifier only includes four gain amplifiers, it is understood that both fewer and greater numbers of gain amplifiers can be used in the present invention. A multiplexer 1611 selects one output to be sent to an analog to digital converter 1613, thereby providing four levels of conversion gain. This same conversion is also performed for a dark-current correction, thus allowing the integrated value of the PMT dark current to be subtracted from the readings without the occurrence of a flash.

Processor 1601 adjusts PMT power supply 1603 by first measuring a low reference that is contained within a sample well 1121 of carriage 1101 as shown in FIG. 11. Preferably the low reference is a piece of polystyrene. This measurement is used to adjust power supply 1603 so that highest gain ADC 1618 (i.e., 64×) is near a maximum value. Two additional lower PMT voltage levels are then selected so that the gain dynamic range provided by the multiple ADC conversions 1615–1618 overlap when the lower voltage levels are selected. In this manner when a reading at ADC gain 1615 (i.e., 1×) approaches a maximum count, the reading at the high ADC gain level 1618 (i.e., 64×), decremented to the next voltage level, results in a reading slightly lower than the maximum count.

Each sample well of multi-assay plate 111 can be irradiated several times, the results of separate readings (i.e., each "reading" comprises irradiation and signal measurement steps) being averaged to provide an average sample well reading. Due to the PMT dark current characteristic, a targeted precision level can be achieved by averaging fewer readings at higher signal levels than would be required at lower signal levels. Therefore samples with different sample intensities may be irradiated a different number of times where the number of readings is inversely proportional to the square root of the sample intensity.

Figure 17:
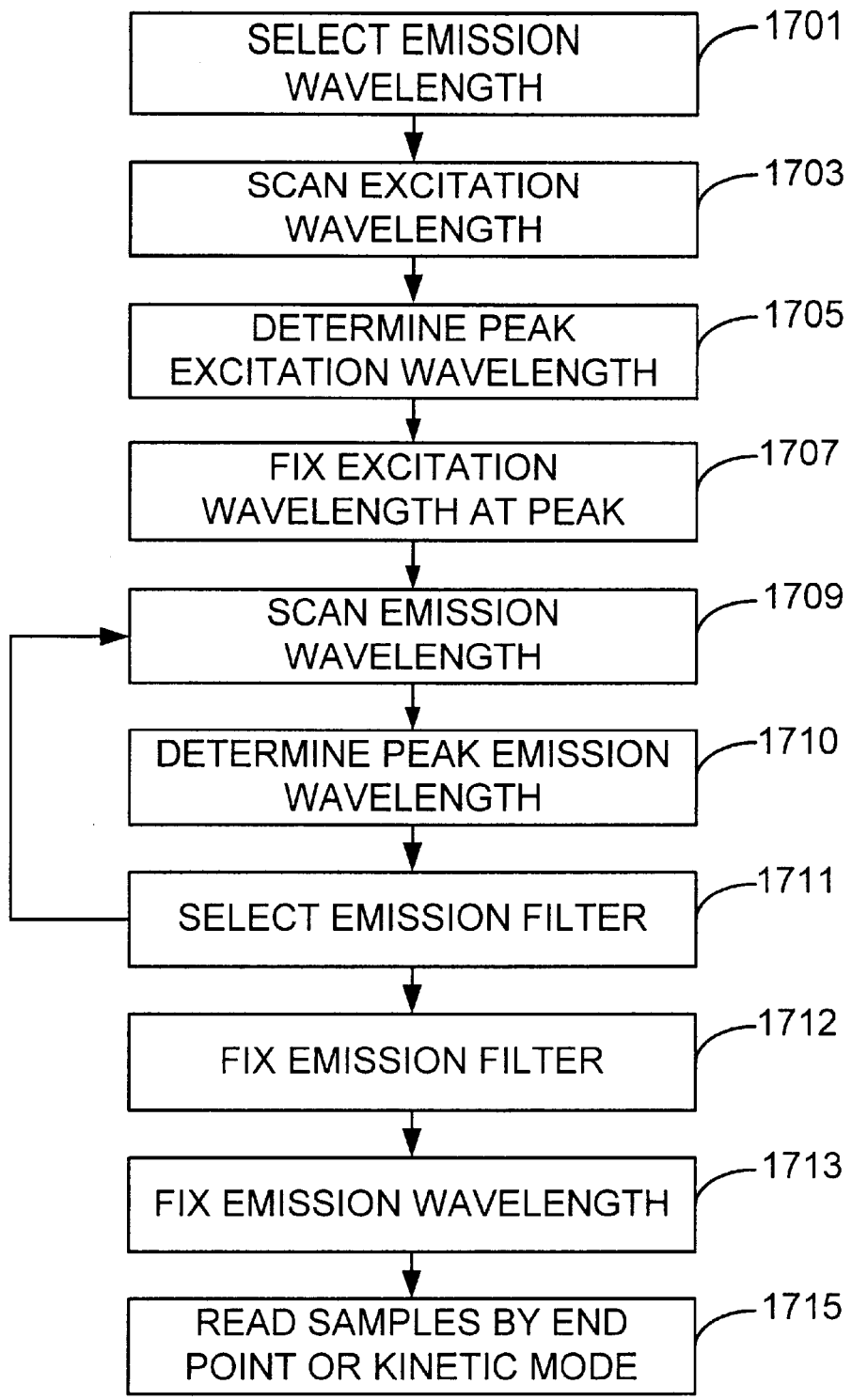
FIG. 17 is a block diagram outlining the wavelength optimization procedure.

When used as a fluorometer for end-point or kinetic measurements, the preferred embodiment of the invention first optimizes the selected excitation and emission wavelengths by using the procedure illustrated in FIG. 17. The first step is to select an emission wavelength between about 20 and 50 nanometers, and preferably about 35 nanometers, higher in wavelength than the expected emission peak (step 1701). The excitation wavelength is then scanned up to within approximately 20 nanometers of the fixed emission wavelength (step 1703). The observed peak excitation is determined from this scan (step 1705) and the excitation wavelength is fixed at this wavelength in at least one embodiment of the invention (step 1707). Alternatively, the excitation wavelength may be fixed at the leading edge of this wavelength, at approximately the 90 percent maximum. The latter approach is optimal when the difference between the excitation and emission peaks is small, i.e., less than 50 nanometers. The emission wavelength is then scanned (step 1709) and the observed peak emission wavelength is determined (step 1710). Next, the emission filter is selected (step 1711). Although a default filter can be selected as previously described, in the preferred embodiment the emission filter is selected by trial and error, thus requiring the repetition of steps 1709–1711 as shown. In the preferred approach, step 1711 (i.e., selection of the cutoff emission filter) is achieved through comparison of the spectrum obtained from two samples representing "signal" (i.e., signal due to a high concentration fluorophore) and "background" (i.e., signal from a sample with no fluorophore) and selection is based on the optimization of the signal-to-background ratio. Still another alternative is to use the default filter selected as previously described.

In the preferred embodiment of the invention, step 1711 is performed using filter wheel 140. Filter wheel 140 includes the available emission cutoff filters 139. Optimally the cutoff value (i.e., the wavelength giving 50 percent maximal light transmission) should be near the maximal emission wavelength, preferably between the excitation wavelength and the maximal emission wavelength, but at least 35 nanometers greater than the excitation wavelength. In the preferred embodiment, the cutoff filter values are 420, 435, 455, 475, 495, 515, 530, 550, 570, 590, 610, 630, 665, and 695 nanometers. Preferably there is one filter position on both filter wheels 140 and 108 that is left open, i.e., with no filter in place, thus providing unlimited light transmission.

After the emission filter is fixed (step 1712), the emission wavelength is fixed at a wavelength approximately 10 nanometers greater than the emission filter cutoff (step 1713). Assuming multiple samples contained in the sample wells of a multi-assay plate, each sample well is then read using the excitation and emission wavelengths selected during the optimization process (step 1715).

In a typical fluorometer, the detected fluorescence is not simply a function of the quantity of the fluorescing material. Rather, the detected fluorescence is also affected by detector sensitivity, detector drift, source intensity (unless the source is referenced), volume of the sample that is excited (i.e., beam size and path length), and monochromator and/or filter efficiency. In order to compensate for these factors, the present invention uses a pair of built-in fluorescence references referred to herein as a high reference and a low reference. The high and low references are 1123 and 1121, respectively, included in a portion of carriage 1101 as shown in FIG. 11. The low reference is a clean piece of polystyrene.

In the present invention, fluorescence is calculated in terms of Relative Fluorescence Units (RFU). A RFU is defined as:

$$RFU \equiv \frac{(\text{PMT cal. coeff.})(\text{PMT signal})(\text{Ref. sens. coeff.})}{(\text{Filtertrans})(\text{Ref. signal})(e^{PMT\,voltage})(\text{PMT sens. coeff.})}$$

where:

PMT cal. coeff.—The PMT calibration coefficient is determined by measuring the high reference at specific excitation and emission wavelengths and at constant, predetermined, PMT voltage and amplifier gain settings. Preferably the excitation and emission wavelengths are 423 and 525 nanometers, respectively, and no emission filter 139 is used during the measurement. Once this coefficient is measured for these excitation and emission wavelengths, it is used for measurements made at all excitation and emission wavelengths. Generally, emission and excitation wavelengths are continuously selectable between 250 and 850 nanometers and are settable in 1 nanometer increments.

PMT signal—The PMT signal is the measured intensity of the emission from the sample in question. It is determined from the PMT ADC counts by subtracting the PMT ADC counts before the flash from the PMT ADC counts after the flash (i.e., difference between post and pre counts for the sample).

Ref. sens. coeff.—The reference sensitivity coefficient is the sensitivity of the reference detector (i.e., detector 2409 in FIG. 24) as a function of excitation wavelength. Although this coefficient may be derived from an equation, in the preferred embodiment a look-up table contained within the system memory is used. Table 3 below provides the reference sensitivity coefficient for the preferred embodiment, as a function of excitation wavelength. Coefficients for intermediate wavelength values are obtained by linear interpolation.

TABLE 3

| Excitation Wavelength (nm) | Reference Sensitivity Coefficient |
| --- | --- |
| 200 | 0.25 |
| 300 | 0.25 |
| 400 | 0.50 |
| 500 | 0.77 |
| 600 | 0.95 |
| 700–850 | 1.07 |

Filter trans—The filter transmission value is the maximum transmission value for a particular emission filter. Preferably these transmission values are contained within a look-up table contained within the system memory. Table 4 below contains the maximum transmission value for each of the emission filters shown in Table 2.

TABLE 4

| Filter No. | Filter Transmission |
| --- | --- |
| 1 | 1.0 |
| 2 | 0.89 |
| 3 | 0.88 |
| 4 | 0.86 |
| 5 | 0.88 |
| 6 | 0.89 |
| 7 | 0.89 |
| 8 | 0.89 |
| 9 | 0.92 |
| 10 | 0.90 |
| 11 | 0.91 |
| 10 | 0.91 |
| 13 | 0.91 |
| 14 | 0.92 |
| 15 | 0.92 |

Figure 24:
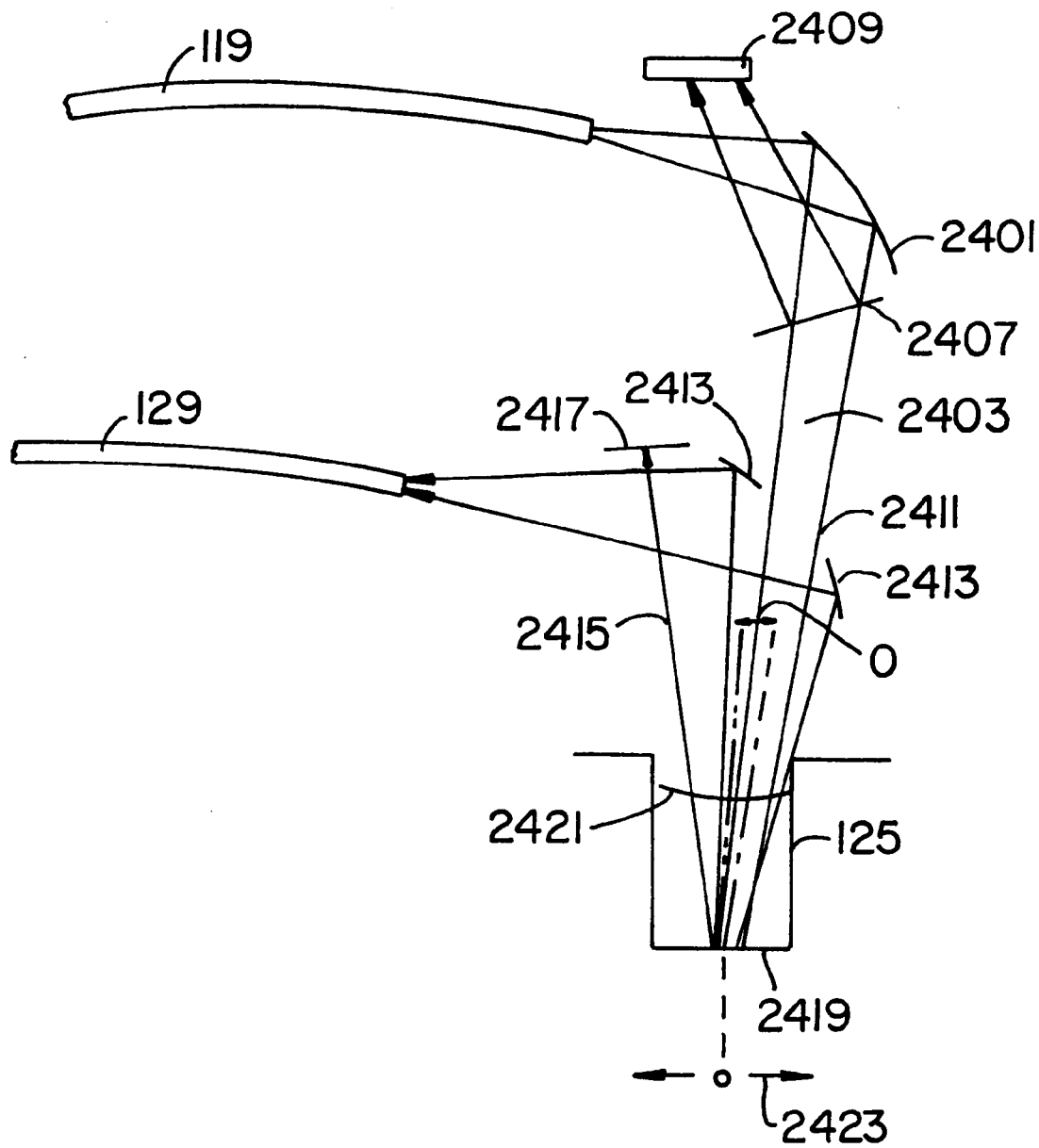
FIG. 24 schematically illustrates the well optics.

Ref. signal—The reference signal is the signal received from the reference detector which measures relative excitation light intensity (i.e., detector 2409 in FIG. 24).

$e^{PMT\,voltage}$—This value compensates for the gain of the PMT as a function of voltage. In the preferred embodiment a predetermined equation approximating the PMT manufacturer's published specifications is used to establish this value.

PMT sens. coeff.—The PMT sensitivity coefficient is the sensitivity of the PMT as a function of emission wavelength. Although this coefficient may be derived from an equation, in the preferred embodiment a look-up table contained within the system memory is used. Table 5 below provides the PMT sensitivity coefficient for the preferred embodiment, as a function of emission wavelength. The values contained in Table 5 are taken from the manufacturer's published spectral response of the PMT used in the system. Coefficients for intermediate wavelength values are obtained by linear interpolation.

TABLE 5

| Emission Wavelength (nm) | PMT Sensitivity Coefficient |
|---|---|
| 300 | 0.6 |
| 400 | 0.7 |
| 500 | 0.95 |
| 600 | 0.78 |
| 700 | 0.54 |
| 800 | 0.4 |
| 900 | 0.27 |

In addition to the above, a calibration routine can be used to improve the accuracy associated with changes in the PMT voltage. Normally the voltage versus sensitivity characteristic of the PMT is an exponential function. Unfortunately, 2 percent fit errors are not uncommon with a voltage change. In a preferred embodiment of the invention these errors are eliminated by making small changes in the PMT voltage and measuring the actual voltage versus gain curve for a given PMT under measured conditions. These measurements may be made at the preselected emission wavelength of interest and desired light intensity level by adjusting the excitation wavelength suitably near the emission wavelength to provide the desired intensity of reflected (and Rayleigh scattered) stray light from low reference 1121.

Further refinement can be achieved through the use of a PMT matching coefficient. The matching coefficient is intended to compensate for variations in PMT sensitivity as the voltage of the PMT is changed, for example during incremental voltage changes when the system is operating in the automated emission or excitation spectrum mode. The matching coefficient is defined as the calculated RFU at the first voltage divided by the calculated RFU at the second voltage. In at least one embodiment a table of matching coefficients is determined which can then be applied to subsequent sample scans.

Operational Modes

Figure 18:
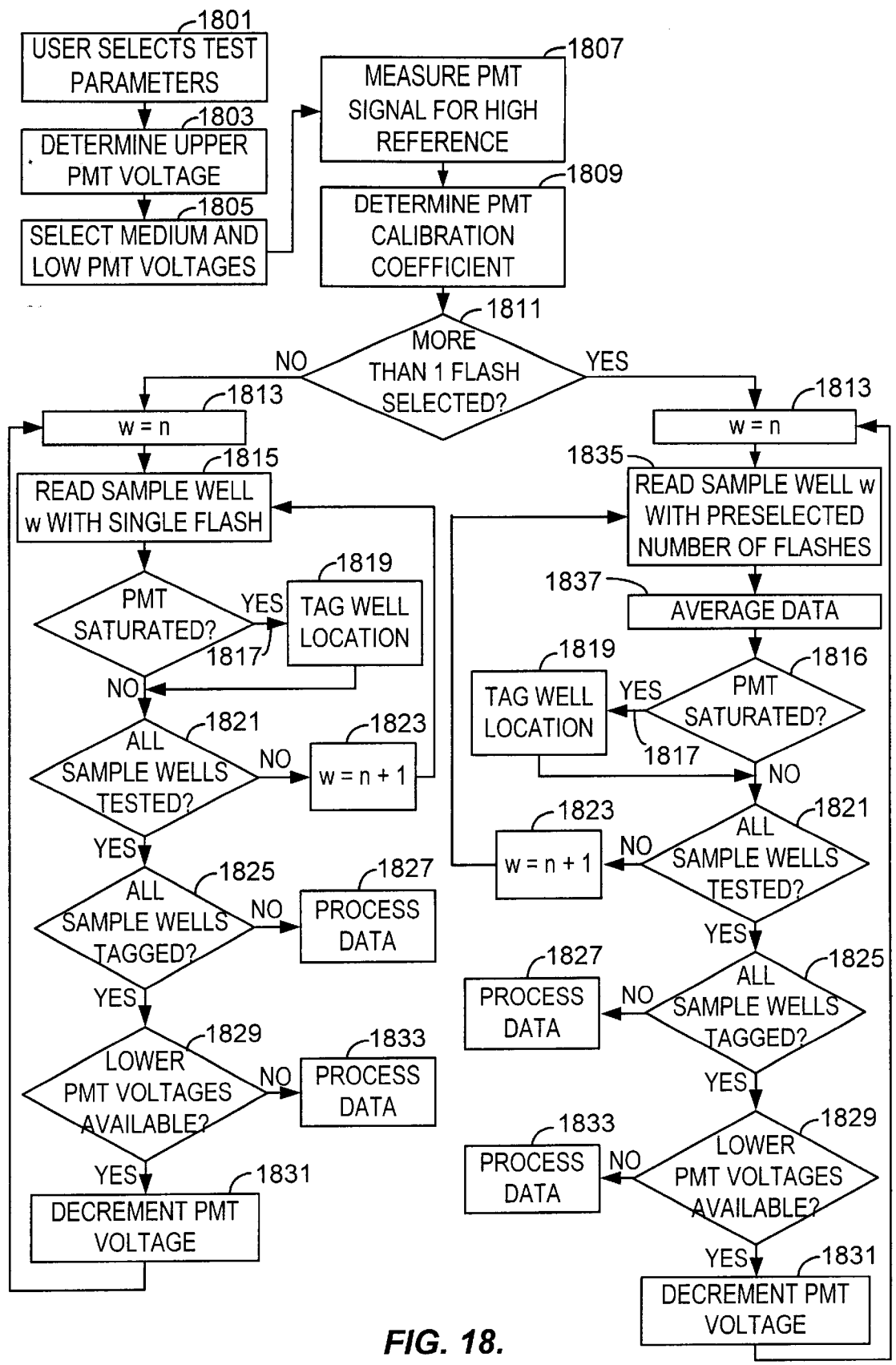
FIG. 18 illustrates the algorithm used when a plate is read using the automatic mode of the invention.

When one or more samples in a multi-assay plate are irradiated and the resulting fluorescent light collected and quantitated the plate is said to be "read." FIG. 18 illustrates the algorithm used when a plate is read using the automatic mode described briefly above. The first step, regardless of the mode of operation, is for the user to enter or select the various testing parameters (step 1801). For example, the user would select the mode (e.g., automatic, manual) and depending upon the mode, other parameters such as the excitation wavelength, the emission wavelength, the number of flashes per well, the emission cutoff filter, etc. The upper voltage for the PMT is then automatically determined by measuring the PMT signal of the low reference (step 1803). Based on the experimentally determined voltage, medium and low PMT voltages are then selected (step 1805). Although the preferred embodiment of the invention utilizes three voltage levels, both fewer and greater numbers of voltage levels can be used.

After the PMT voltages have been set, the PMT signal is measured for a high reference (step 1807) at the wavelengths specified for the high reference in order to determine the PMT calibration coefficient (step 1809). High reference 1123 is a stable fluorescent material such as can be obtained from Spec Check of Fullerton, Calif. and is contained in carriage 1101 as shown in FIG. 11.

The next step is to read the sample plate, assuming that the user selected a sample plate rather than a cuvette for analysis in step 1801. Prior to reading the plate, the system determines if the user had initially selected more than a single flash per sample well (step 1811). If the user had initially selected a single flash per well, the sample plate and optics are moved to the first location, i.e., w=n (step 1813) and the sample well is read with a single flash from flash lamp 103 (step 1815). During the first scan of the sample plate the PMT is set at the high voltage, assuming that the user has not pre-selected a specific PMT voltage. In step 1815 four ADC gain conversions are calculated using gain amplifiers 1115–1118 for the sample measurement. Gain multiplexer 1111 selects the output from the gain amplifier that has the highest gain and yet is below the saturation level, passing the selected value on to system processor 1101 for further processing. If none of the outputs for a particular sample well are below the saturation level (step 1817), the sample well is tagged for further analysis by temporarily storing the location of the well in memory.

After a sample well has been tested, the system determines whether the entire sample plate has been tested (step 1821). If there are more sample wells to be tested, the sample location is changed, i.e., n is increased by 1 (step 1823) and the next sample well is tested. If all of the sample wells have been analyzed, the system determines whether or not any sample wells were tagged (step 1825). If there are no tagged sample wells, the data is processed (step 1827). If there are any tagged sample wells, the system determines whether there is a lower PMT voltage available (step 1829) and if there is, the PMT voltage is decremented (step 1831) and the sample reading process starts over. Although all of the sample wells can be read at the lower PMT voltage, in the preferred embodiment only those samples that were previously tagged are read at the lower voltage. If the system determines at step 1829 that there are no lower PMT voltages available, the data are processed (step 1833), noting those samples in which the PMT was saturated for all voltages. During the data processing steps (i.e., steps 1827 and 1833), preferably a table of RFU values for all of the sample wells is determined, although the data can be calculated and provided to the user in other formats (e.g., plots, graphs, etc.). The intensity values for the wells are normalized in accordance with the differences in PMT voltage.

If step 1811 determines that more than 1 flash has been selected, the procedure for sample testing is basically the same as for the single flash process with one notable exception. During sample testing, each sample well is illuminated by flash lamp 103 with the preset number of flashes (step 1835). The data from these readings are then averaged (step 1837). In the preferred embodiment of the invention, during step 1835 if the PMT saturates after the first flash, the preset number of flashes is over-ridden for the sample well in question, limiting the number of flashes to one.

Figure 19:
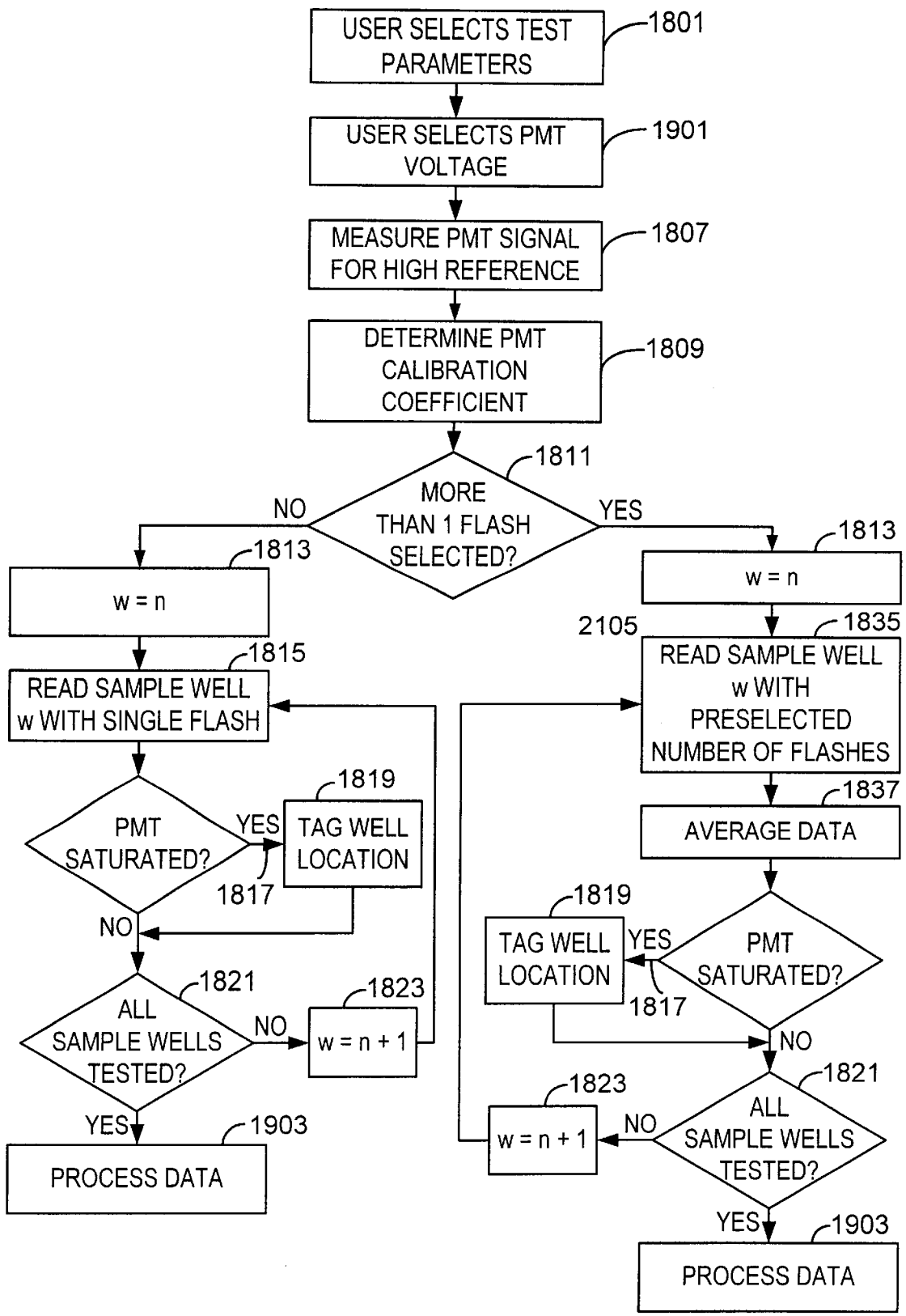
FIG. 19 illustrates an alternative approach to the technique shown in FIG. 18.

FIG. 19 illustrates an alternative approach to the technique shown in FIG. 18. As in the previous approach, the user first enters various testing parameters (step 1801). In addition, the user selects a PMT voltage (step 1901). The user may be provided with three pre-selected voltages to chose from, or the user may be given a range of voltages from which to select. The rest of the process is the same as that described with reference to FIG. 18 except that the PMT voltage is not lowered after all of the samples have been tested. Rather, after the plate is read, the data are simply processed (step 1903).

Figure 20:
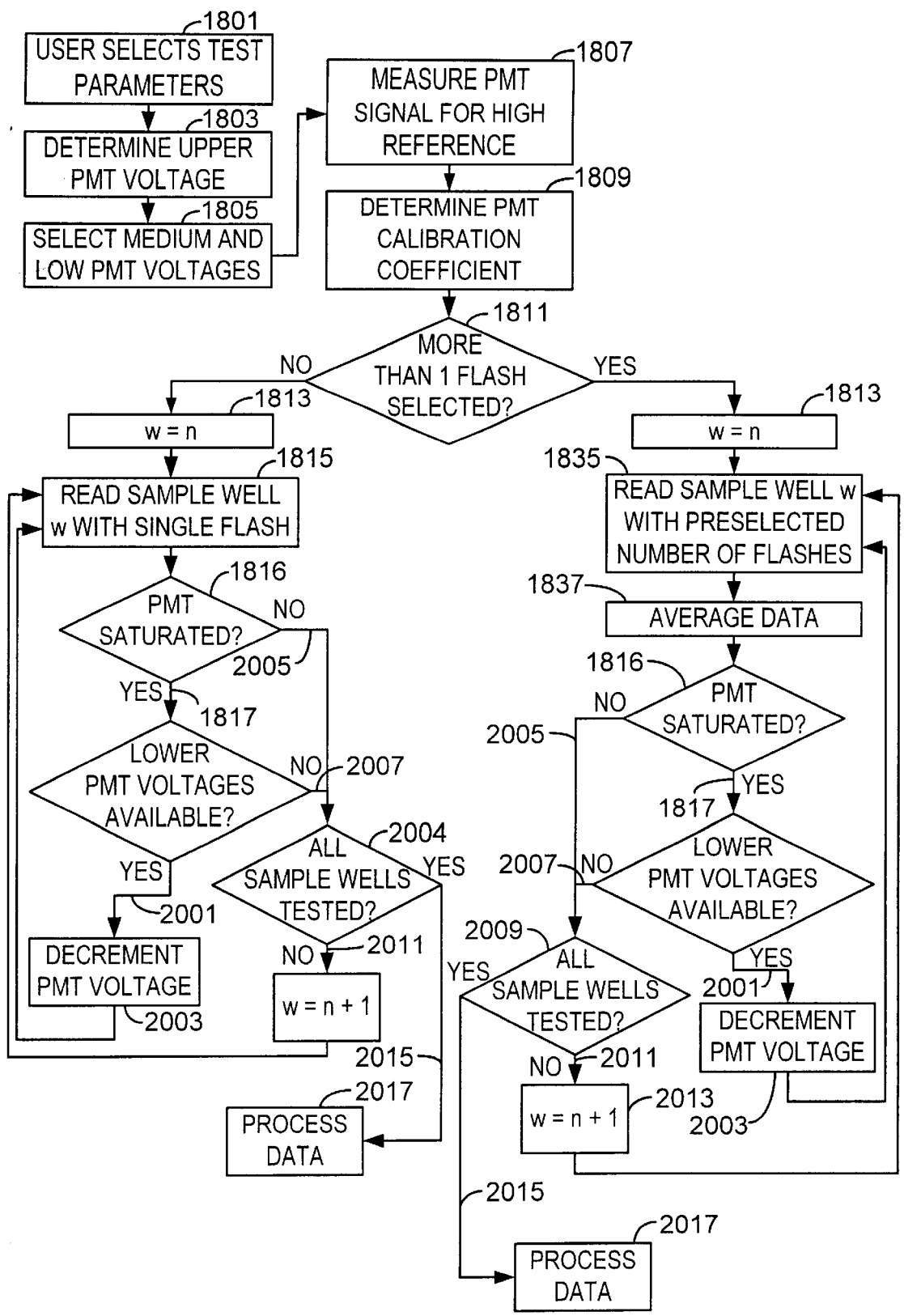
FIG. 20 illustrates a variation of the method illustrated in FIG. 18.

FIG. 20 illustrates a variation of the method illustrated in FIG. 18. The steps in this variation are the same as in the FIG. 18 illustrated method up to and including step 1816. In the approach shown in FIG. 18, at step 1816 if the system determines that the PMT is saturated (step 1817) then the sample well is tagged for further analysis in a subsequent scan of the sample plate at a lower voltage. In contrast, in the approach shown in FIG. 20, if the system determines that the PMT is saturated (step 1817) and that a lower PMT voltage is available (step 2001), the PMT voltage is decremented (step 2003) and the sample is re-tested. Re-testing of the sample at incrementally lower PMT voltages continues until either the PMT is not saturated (step 2005) or there are no lower PMT voltages available (step 2007). At that time the system determines whether or not there are any more samples to be tested (step 2009). If more samples remain (step 2011) then the process repeats itself for the next sample (step 2013). Once all of the samples have been tested (step 2015), the data are processed (step 2017) as previously described. The same technique of testing a sample at multiple PMT voltages, if required, prior to moving to the next sample is also used for samples in which more than 1 flash was selected.

Figure 21:
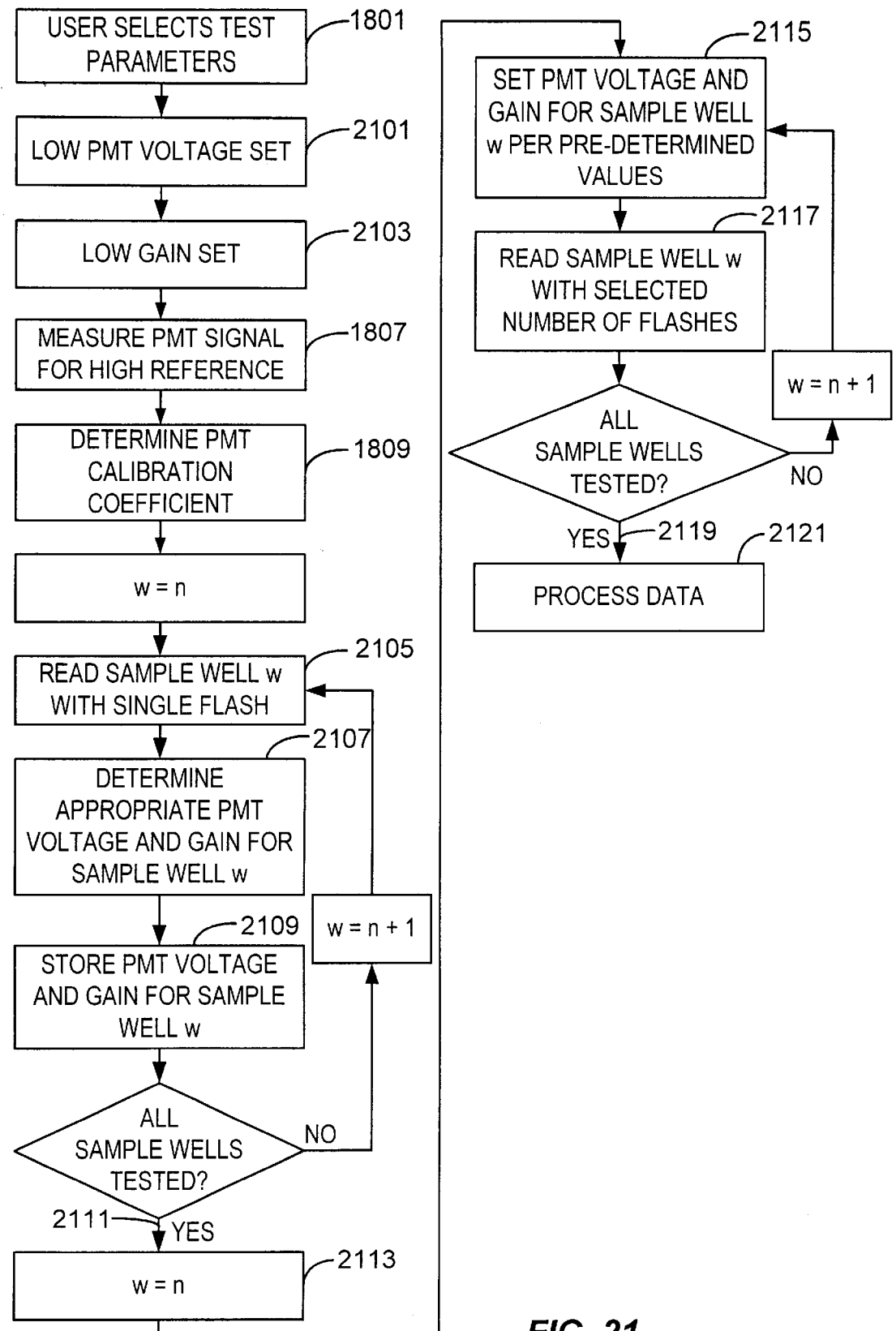
FIG. 21 illustrates another approach that may be utilized by the present invention.

FIG. 21 illustrates another approach that may be utilized by the present invention. In this approach, termed a fly-by technique, a cursory review of all of the samples within a sample well is performed prior to the detailed analysis of the samples. As in the prior approaches, the user initially enters the data required by the system (step 1801), including the selection of the fly-by approach. The system then sets the PMT voltage at a low level (step 2101) and the gain at a low level (step 2103). After measuring the high reference (step 1807) and setting the PMT calibration coefficient (step 1809), the signal from the first sample well is read (step 2105). Based on this signal, the appropriate PMT voltage and gain setting for this sample are determined (step 2107) and recorded (step 2109). This process continues, sample by sample, until all of the sample wells have been tested (step 2111). Sample testing then starts over (step 2113). For each sample the PMT voltage and gain are set according to the pre-determined values (step 2115) and the sample is tested (step 2117). Once all of the samples have been tested (step 2119), the data is processed (step 2121).

Figure 22:
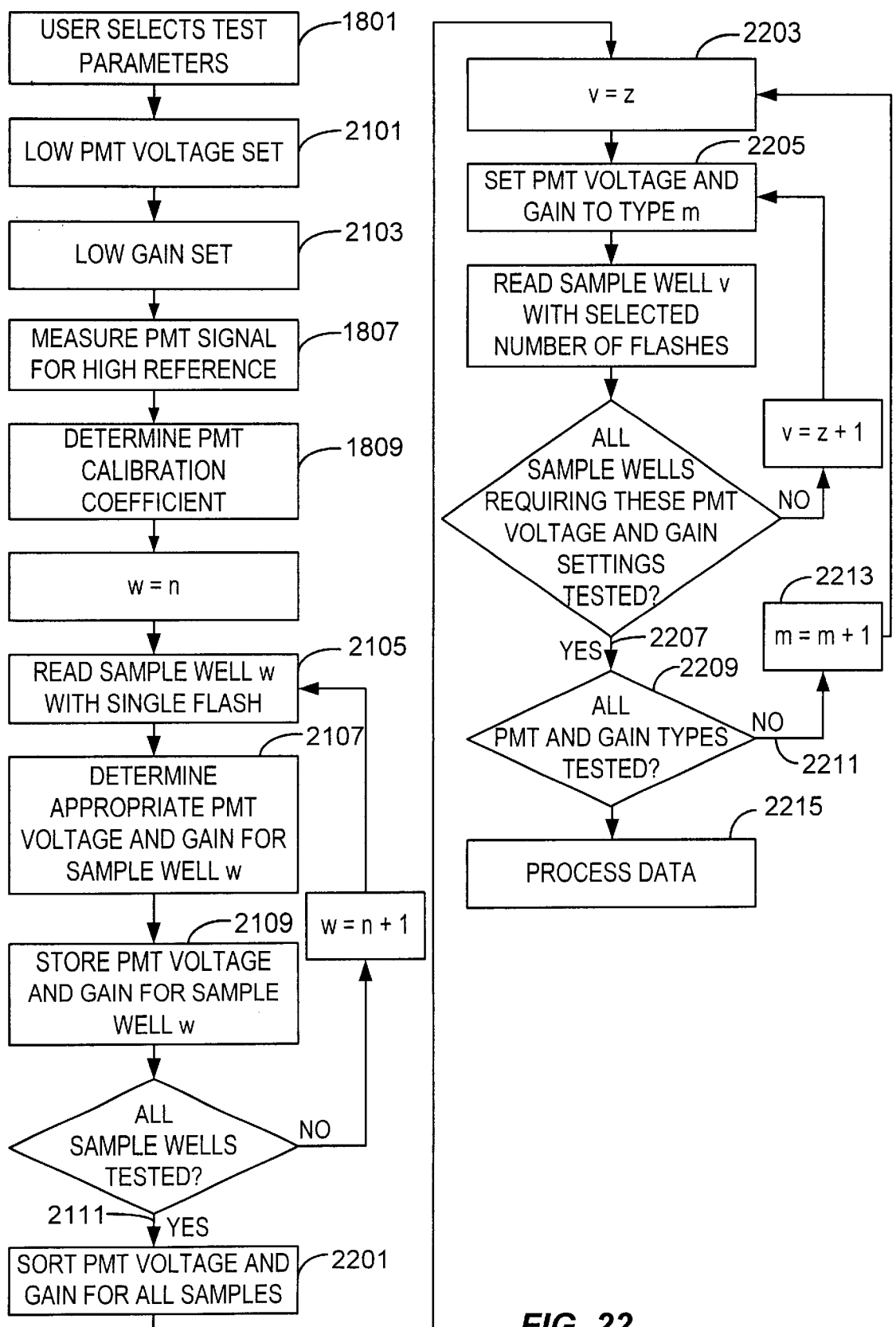
FIG. 22 illustrates a slight variation of the method shown in FIG. 21.

FIG. 22 illustrates a slight variation of the method shown in FIG. 21. As in the previous example, all of the samples are initially tested with a single flash with low PMT voltage and gain settings in order to determine the appropriate PMT voltage and gain for a specific sample. In this method, however, after the initial testing of all of the samples (step 2111) the samples are sorted according to the determined PMT voltage and gain settings (step 2201). Thus all samples requiring PMT voltage "x" and gain "y" are placed in one bin, etc. Sample testing then starts (step 2203) with the PMT voltage and gain set at a first setting (step 2205). After all of the samples that were identified in steps 2107 and 2201 as requiring these PMT voltage and gain settings are tested (step 2207), the system determines whether there are samples requiring other PMT voltage and gain settings (step 2209). If some of the samples remain untested (step 2211), the settings are changed (step 2213) and all of the samples requiring the new settings are tested. Once all of the samples have been tested the data are processed (step 2215).

Alternatively, the samples are sorted only according to PMT voltage required in step 2201 (i.e., not according to gain). Subsequent steps shown in FIG. 22 remain the same except that multiplexer 1611 automatically selects the appropriate gain as previously described.

Figure 23:
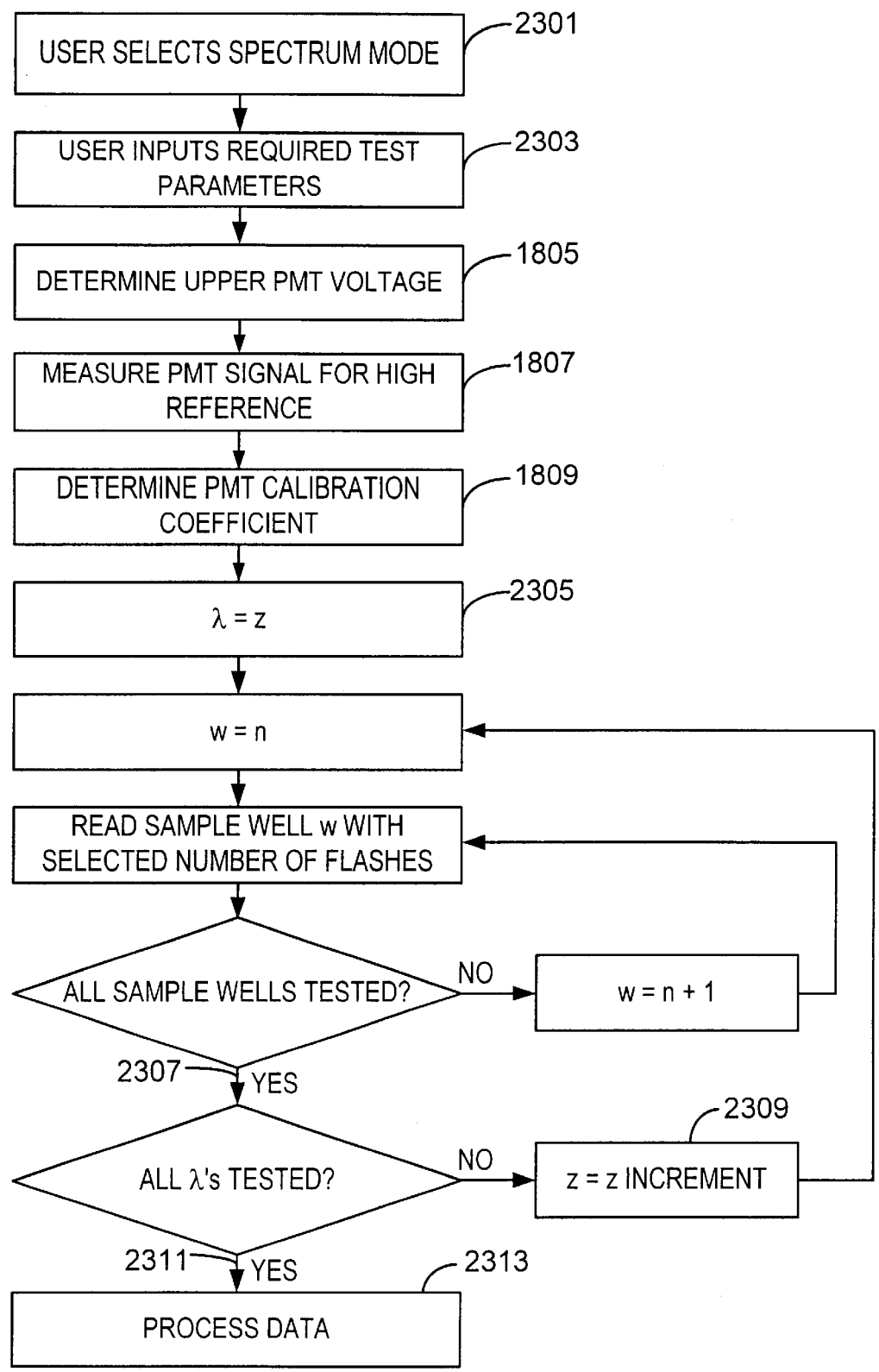
FIG. 23 illustrates a spectrum mode of analysis for use with the invention.

FIG. 23 illustrates the spectrum mode of analysis. To implement this form of analysis, the user selects the spectrum mode during the initial data entry step (step 2301). Once the spectrum mode is selected, the user must input information in addition to that normally required (step 2303). For example, the user may be required to input whether to scan excitation or emission wavelength, starting and stopping wavelengths, and the size of the wavelength increments to be used. Additionally, the user may be required to choose between inputting a specific PMT voltage, selecting a predetermined voltage level (e.g., low, medium, high), or allowing the system to automatically determine the optimal voltage setting. In the auto mode, although the voltage may be varied between three levels as described above with reference to FIG. 18, preferably the voltage is varied in 25 volt increments. In some embodiments increments of a different size can be selected by the user.

Typically in the spectrum mode the system still determines an upper PMT voltage (step 1803) and measures the PMT signal for a high reference (step 1807) in order to determine the PMT calibration coefficient (step 1809). The wavelength is then set at a first wavelength (step 2305) and each of the sample wells is read at this wavelength until all of the samples have been read (step 2307). The wavelength is then incremented (step 2309) and the samples are re-tested. This process continues until all of the samples have been tested for all of the wavelengths of interest (step 2311). The data are then processed (step 2313) and displayed as either excitation or emission spectra for each sample tested.

As noted above, during the spectrum scan the PMT voltage can either be held at a predetermined voltage or level, or the system can operate in an automatic mode where the voltage is optimized. In another variant of the spectrum scanning mode illustrated in FIG. 23 the spectrum for a sample is determined prior to moving to the next sample. Thus, instead of scanning (i.e., reading the plate) all of the sample wells at a single wavelength, incrementing the wavelength, and repeating the plate reads until all of the wavelengths have been scanned, each sample can be individually scanned at the predetermined wavelength values.

Well Optics

The preferred embodiment uses mirrored optics to guide the source light into the selected wells of the multi-assay plate and to guide the emitted light out of the selected wells. The use of mirrored optics enhances the sensitivity of the instrument while reducing the background.

FIG. 24 is a schematic representation of the mirrored optics used to illuminate sample well 125 of a multi-assay plate and to receive the emitted light from the well. The source light passes through fiber 119 to an elliptical focussing mirror 2401. The reflected light follows optical paths 2403 to a sample well 125. A portion of the source light is reflected by beamsplitter 2407 into a reference detector 2409. Detector 2409 is used to monitor the output of source 103, thereby allowing the intensity of the excitation beam to be normalized. In order to illuminate sample well 125, thereby stimulating the emission of fluorescence, phosphorescence, and/or scattered light, the light reflected by mirror 2401, and transmitted through (i.e., not reflected) beamsplitter 2407, passes through an aperture 2411 in a second elliptical focussing mirror 2413. Preferably less than 10 percent of the light in optical paths 2403 is allowed to strike mirror 2413. The light emitted by the sample within well 125 is reflected by mirror 2413 and focussed into detection fiber 129. Specularly reflected light from liquid meniscus 2421 of a liquid sample in well 125 and from the well bottom surface 2419 (e.g., the light following optical path 2415) is trapped by one or more light traps 2417 which are constructed of anodized aluminum. Preferably mirrors 2401 and 2413 are elliptical focusing mirrors, although they may be flat, spherical, or otherwise curved. It will be appreciated by those of skill in the art that mirror 2401 can be replaced by a lens, the lens either being separate from, or attached directly to, the end of fiber 119. The light from the lens, as with mirror 2401 in the preferred embodiment, passes through aperture 2411 of mirror 2413 prior to impinging upon the sample.

Significantly, aperture 2411 in mirror 2413 allows any preselected wavelength of excitation light, which in the preferred embodiment is selected from the range of 250 to 850 nanometers, to pass through the aperture and impinge on the samples contained in sample wells 125. Furthermore, aperture 2411 is relatively small compared to the surface area of mirror 2413. In the preferred embodiment, the area of aperture 2411 is less than 10% of the area of mirror 2413. More generally, the area of aperture 2411 is less than 50% of the area of mirror 2413.

The preferred embodiment of the invention advantageously allows greater than 90% of the available excitation light energy to impinge upon the samples within sample wells 125. This embodiment also allows greater than 90% of the light emitted from the samples within a solid angle subtended by the perimeter of mirror 2413 to be focused directly onto a photodetector, or, in the preferred embodiment, focused onto collection optical fiber 129 which transmits the emitted light to detector 135. Thus the design gives exceptionally efficient utilization and collection of light energy while also allowing wide flexibility in the range of operable wavelengths.

Figure 25:
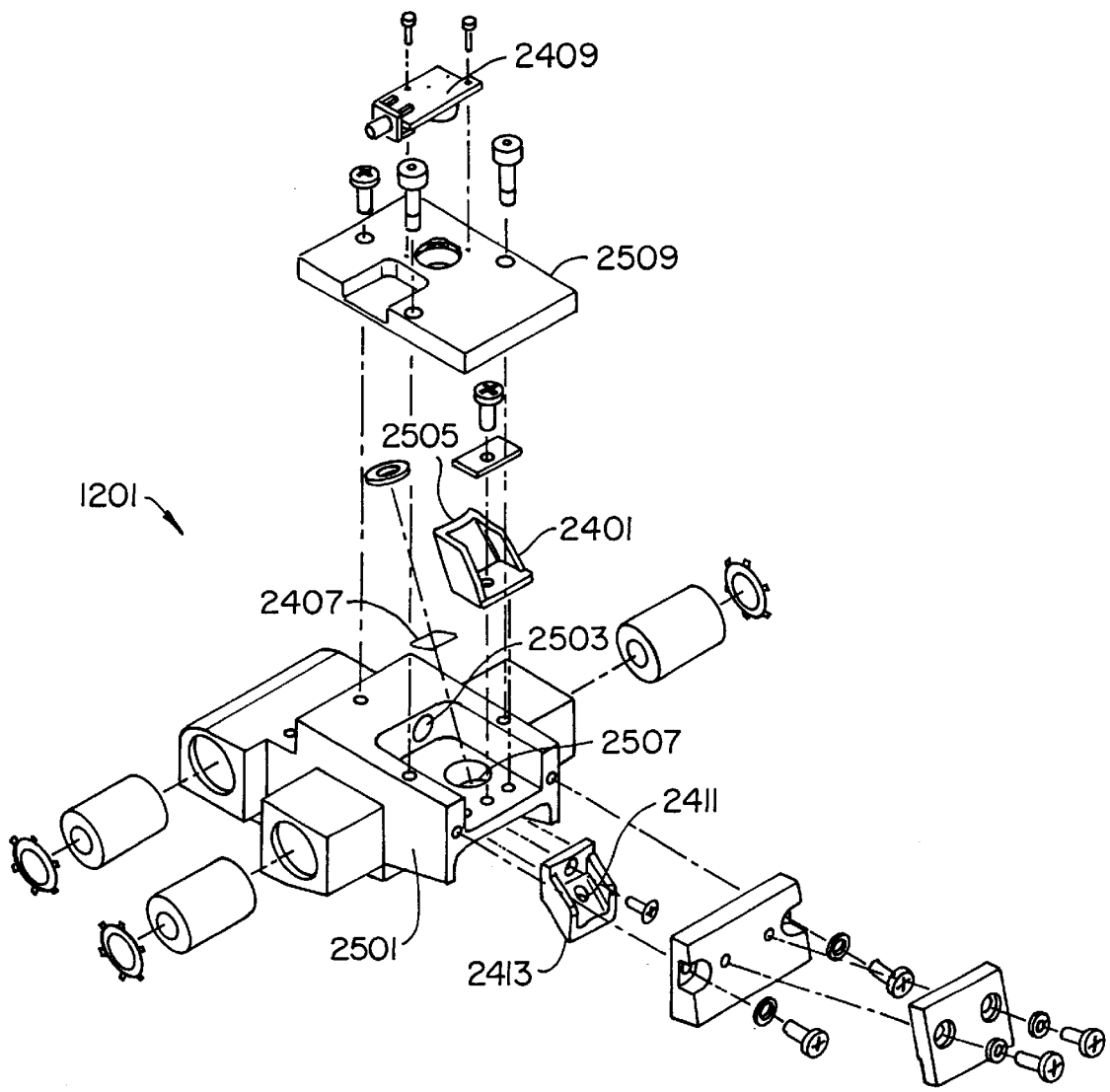
FIG. 25 is an exploded view of an optical scanning head according to the preferred embodiment of the invention.
Figure 26:
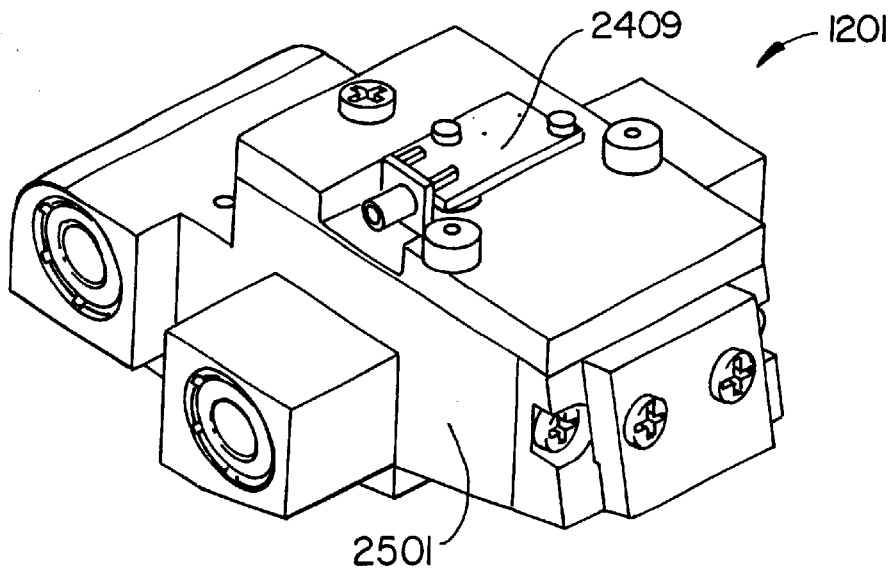
FIG. 26 is a perspective upper view of the optical scanning head shown in FIG. 25.
Figure 27:
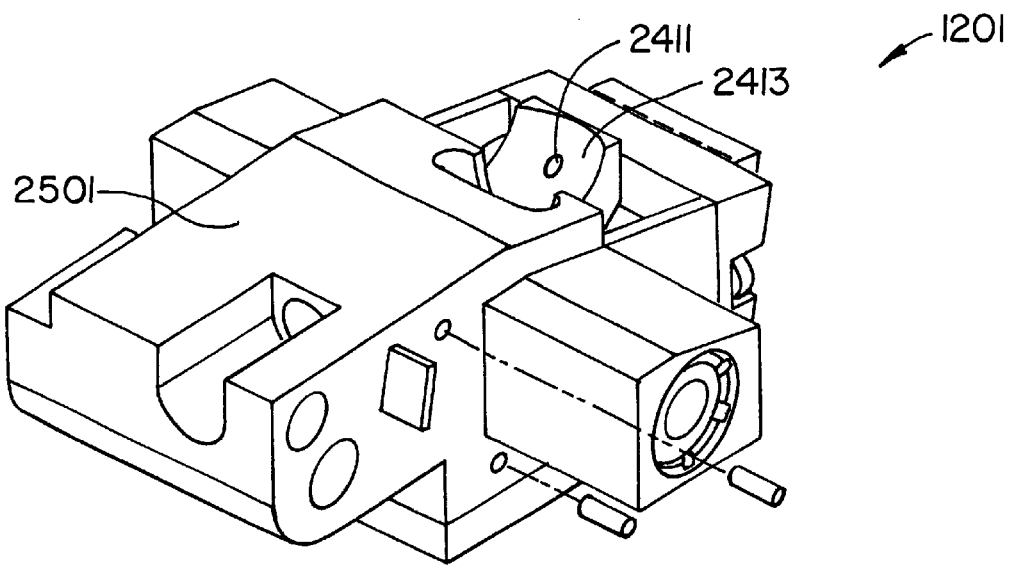
FIG. 27 is a perspective lower view of the optical scanning head shown in FIGS. 25 and 26.

FIG. 25 is an exploded view of optical scanning head 1201. FIGS. 26 and 27 illustrate an upper and lower view, respectively, of the assembled head 1201. Optical source fiber 119 (not shown in this view) is preferably a one millimeter diameter optical fiber. Fiber 119 is attached to head block 2501 such that the source light passes through an aperture 2503 within block 2501. The image of source 103 projected by fiber 119 is magnified and focused a distance 2× in the sample well by a reflective surface 2505 of mirror 2401. The focussed beam passes through an aperture 2507 within block 2501. Beamsplitter 2407, preferably a piece of silica, is fitted within aperture 2507 such that the reflected portion of the source light is detected by detector 2409 fitted to an optical head cover plate 2509. The portion of the focussed beam not reflected by beamsplitter 2407 passes through aperture 2411 of detection mirror 2413. Due to the source beam passing through mirror 2413, this mirror can be located very close to the sample well, thus enabling a high collection numerical aperture (i.e., NA).

Figure 28:
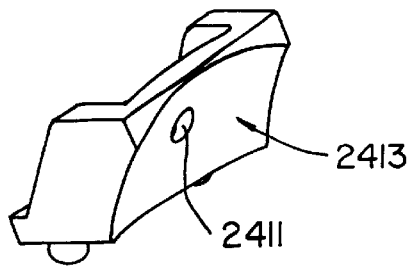
FIG. 28 is a detailed view of the apertured detection mirror used in the preferred embodiment of the optical scanning head.

Mirror 2413 is shown in greater detail in FIG. 28. This mirror has a reversed magnification as compared to source mirror 2401. Thus fiber 119, with a nominal 1 millimeter diameter, corresponds to a 2 millimeter excitation beam at the focal point. This excitation beam generates a 360 degree solid angle emission beam, a portion of which is collected by mirror 2413 and translated into a 4 millimeter image that is projected onto the entrance aperture of emission fiber 129. A small fraction (i.e., less than 10%) of the emission light passes through aperture 2411 and is not collected at emission fiber 129. The ratio of excitation light power passing through aperture 2411 to that in the emission beam collected by mirror 2413 for a high fluorescent sample is small, generally between 0.1 and 50 percent and preferably between 1 and 5 percent (i.e., emission collection efficiency also generally varies between 0.1 and 50% and preferably between 1 and 5%).

Approximately a 4 millimeter diameter image is projected into collection fiber 129 which is preferably 4 millimeters in diameter. Although this is not the only focal geometry that can be used with the present invention, it is preferred since the 1 millimeter excitation aperture formed by optical fibers 119 corresponds to the maximum energy density attainable with a xenon source/monochromator combination with an approximately 10 nanometer bandpass. Similarly, the 4 millimeter emission aperture 141 corresponds to the typical available aperture for a PMT detector/monochromator combination with the desired 10 nanometer bandpass. The preferred focal geometry also provides for high emission collection efficiency.

In addition to the above noted benefits, apertures 2507 and 2411 help to create a well defined excitation beam, blocking a halo from forming near the beam. Without the aperture a portion of the halo is typically reflected, for example by the walls of the well, contributing to unwanted stray excitation light collected by the collection optics and passed to detector 135. The uniform excitation beam diameter throughout the sample path insures uniformity of detection sensitivity within the sample. Furthermore, as the beam is substantially dispersed rather than tightly focussed to a small spot, inhomogeneous sample photodegradation is minimized.

In the embodiment of the invention illustrated in FIG. 24, the optical paths 2403 are not normal to bottom surface 2419 of sample wells 125 (and are not normal to the support surfaces 1301 of carriage 1101 which supports the multi-assay plate having sample wells 125). Rather, these optical paths are canted by an angle $\theta$ with respect to the normal. Generally angle $\theta$ is between 0 and 30 degrees, and preferably angle $\theta$ is between 8 and 12 degrees. The cant of the optical paths allows reflection of the excitation light beam off of bottom surface 2419 as well as sample meniscus 2421, so as to miss detection mirror 2413. Instead these reflections impinge on light trap 2417. Light trap 2417 is preferably a light absorption baffle. If surfaces 2419 of sample wells 125 are clear, the excitation beam passes through the surface and is either absorbed or reflected away, for example with a black polished reflector (e.g., black glass) as illustrated by component 1119 of FIG. 11. Alternatively, angle $\theta$ may be set at 0 degrees, i.e., normal to bottom surface 2419. A cant of 0 degrees is generally preferably for very small sample wells 125 to minimize light scattering from well edges. This approach may also be preferable for absorption measurements in which the source light passes completely through the sample and is detected by a detection system coupled to the bottom surface of multi-assay plate 111 (see FIG. 1).

Figure 29:
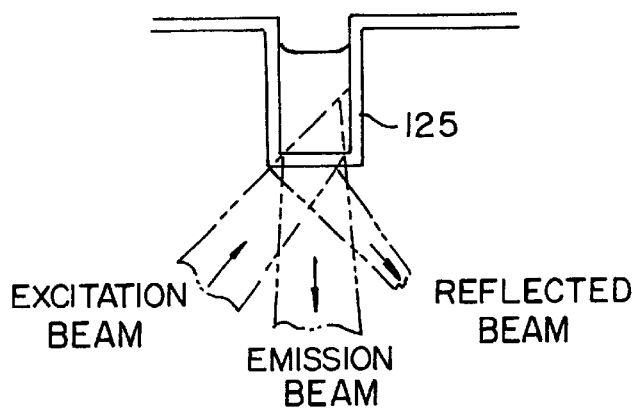
FIG. 29 is an illustration of an alternative optical configuration for use with a sample well.
Figure 30:
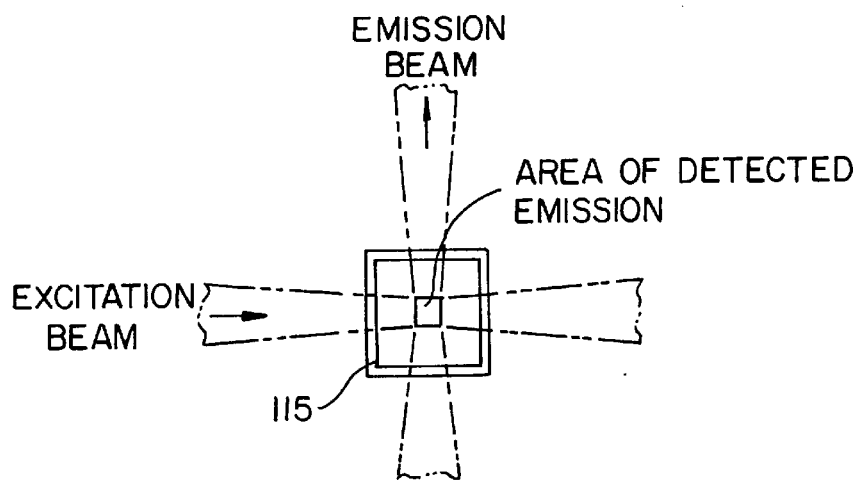
FIG. 30 is an illustration of an alternative optical configuration for use with a cuvette cell.

FIG. 29 illustrates an alternative embodiment of the invention. In this embodiment the excitation beam is projected into sample well 125 through its bottom surface. Similarly, the detected emission from the sample well is also detected through the bottom surface. In order to minimize stray light background from the excitation source entering the detection assembly, the excitation beam is at an angle to the normal to the bottom surface of the well. A cuvette reading embodiment is illustrated in FIG. 30. In this embodiment the excitation beam and the emission beam are substantially orthogonal, thereby minimizing the background.

Besides canting the optical paths by an angle θ as described above with reference to FIG. 24, preferably the system is further optimized by moving the intersection of the optical path of excitation beam 2403 and a plane defined by the top of the sample well away from the sample well's center line. Moving the optical path off center helps to reduce the amount of excitation light that reflects off of sample upper surface 2421 and enters into detection fiber 129. Generally the offset from the center will be between 1 and 40 percent of the well diameter. The offset is particularly effective when combined with canting the optical path by an angle θ as described above.

Several factors determine the distance that excitation beam 2403 should be moved along axis 2423 to minimize undesired reflections. First, due to the angular dependence of the reflections from surface 2421, the amount of cant angle θ is critical. Generally, greater values of cant angle θ will require greater offset distance from the center. Second, the curvature of meniscus 2421 is integral to determining where incident beam 2403 is reflected. The curvature depends upon the diameter and shape of the sample well and the characteristics (e.g., interfacial tension) of the sample with the walls of sample well 125.

Figure 31:
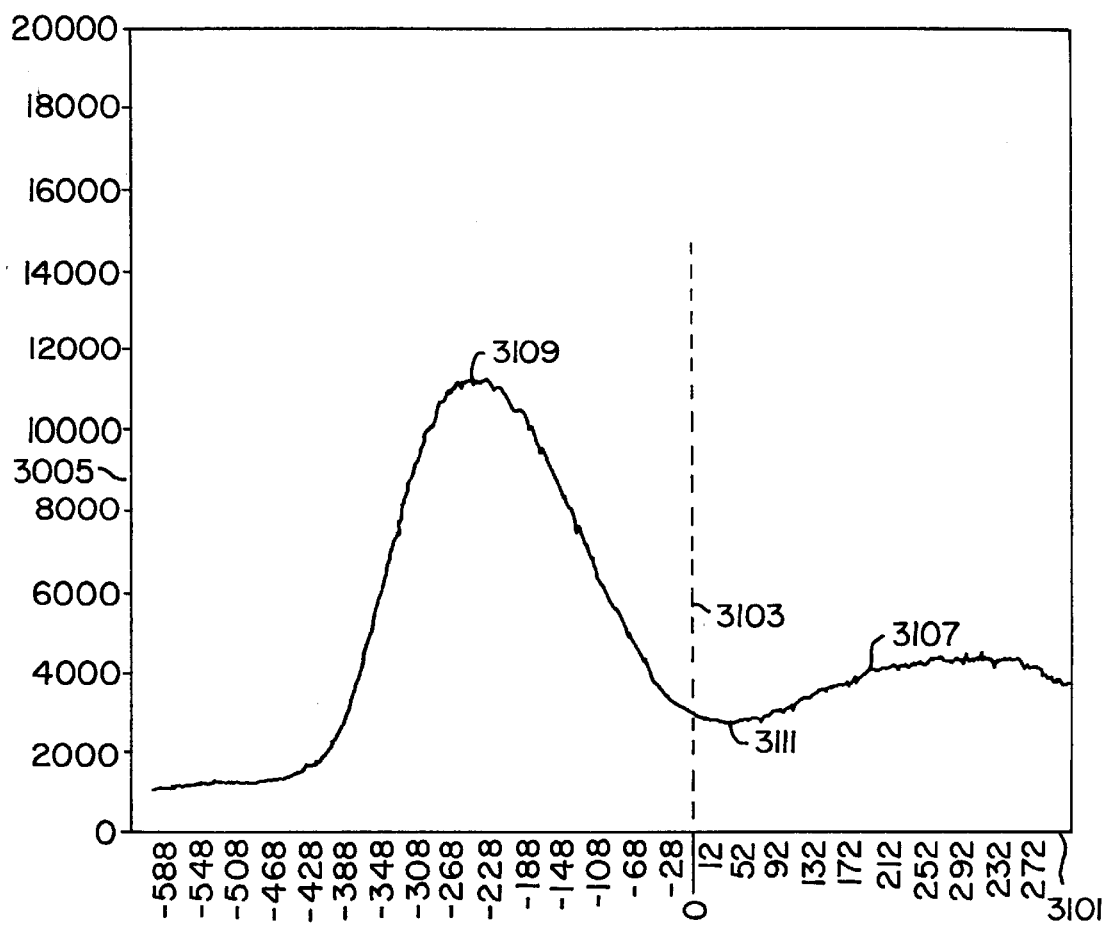
FIG. 31 illustrates the relationship between the position of the excitation light in the sample ell with the amount of light reflected into the detector fiber.

FIG. 31 illustrates the dependence of the amount of excitation light reflected into detector fiber 129 as a function of position. X-axis 3101 shows the position of the incident excitation beam relative to a well center 3103. Y-axis 3105 shows the PMT signal in arbitrary units. Curve 3107 is an example of signal curve for a particular sample plate, sample material, etc. A peak 3109 of curve 3107 is due to the excitation beam being reflected by the meniscus into the detection fiber. A minimum 3111 of curve 3107 indicates the relative distance that the excitation beam should be moved away from well center 3103 in order to minimize reflections and thus optimize the signal to background ratio.

In at least one embodiment of the invention, a look-up table is generated that provides the optimal position of the sample well relative to the excitation beam for a variety of commonly used sample plates. To use the look-up table the user enters the type of sample plate and the system automatically adjusts the well position. Alternately, a user can first set all of the various system parameters such as sample plate type, excitation beam cant angle, etc. and then run a calibration run using a background reference sample in order to determine the optimal well position. Then the sample plate containing the unknowns (i.e., samples) can be run using the same well position.

Time Tagging

Time tagging refers to a method of monitoring the progression of a reaction or of tracking a series of measurements. Therefore this process has greatest utility when the material or composition under investigation is relatively unstable. For example, in a test to determine the absorption properties of a series of materials of slightly differing composition, time tagging is typically not required, assuming that the absorption properties of the materials do not change with time. In contrast, in a luminescence investigation where the luminescence of a material is initiated by the addition of one or more reactants, it may be critical to record the time that the luminescence is measured with respect to the time that the reactants were added. Furthermore, if the luminescent properties of a series of compositions are being compared, a valid comparison may require that the time sequence for each individual composition be recorded. As the number of samples under comparison is increased, for example by using a multi-assay plate with a large number of sample wells, monitoring the reaction kinetics as a function of time becomes increasingly important. Particularly important is the exact amount of time passed between preparation and characterization of each sample. Also, sequential repeating of the characterization process permits kinetic analysis of the processes occurring in the one, or more, samples contained in the wells of a multi-assay plate.

In the preferred embodiment of the invention, the instrument can be operated in several different time tagging modes. Although in the preferred embodiment internal processor 1101 performs the time tagging function, a separate internal processor or an external processor may also perform this function.

The simplest mode of time tagging is to simply assign a single time point for an entire sample series. In this mode a first time is recorded that is representative of the initiation of the experiment. This time point can represent, for example, the addition of a reactant to each material within the sample series. A second time is then recorded when the sample series is characterized (e.g., by measuring fluorescence, luminescence, or absorption). If the sample series is characterized repeatedly over time, each time the series is characterized a time associated with the characterization may be recorded. Thus each of the materials within the series can be characterized as a function of time. Although this mode of time tagging is adequate for many investigations, it does not take into account variations encountered at the onset of the experiment, for example due to the addition of the reactants in a sequential rather than simultaneous fashion. Nor does this mode take into account any time lag associated with the measurement process. This time lag can be substantial for a multi-assay plate with a large number of sample wells (e.g., 364 or 1500 sample wells).

Figure 32:
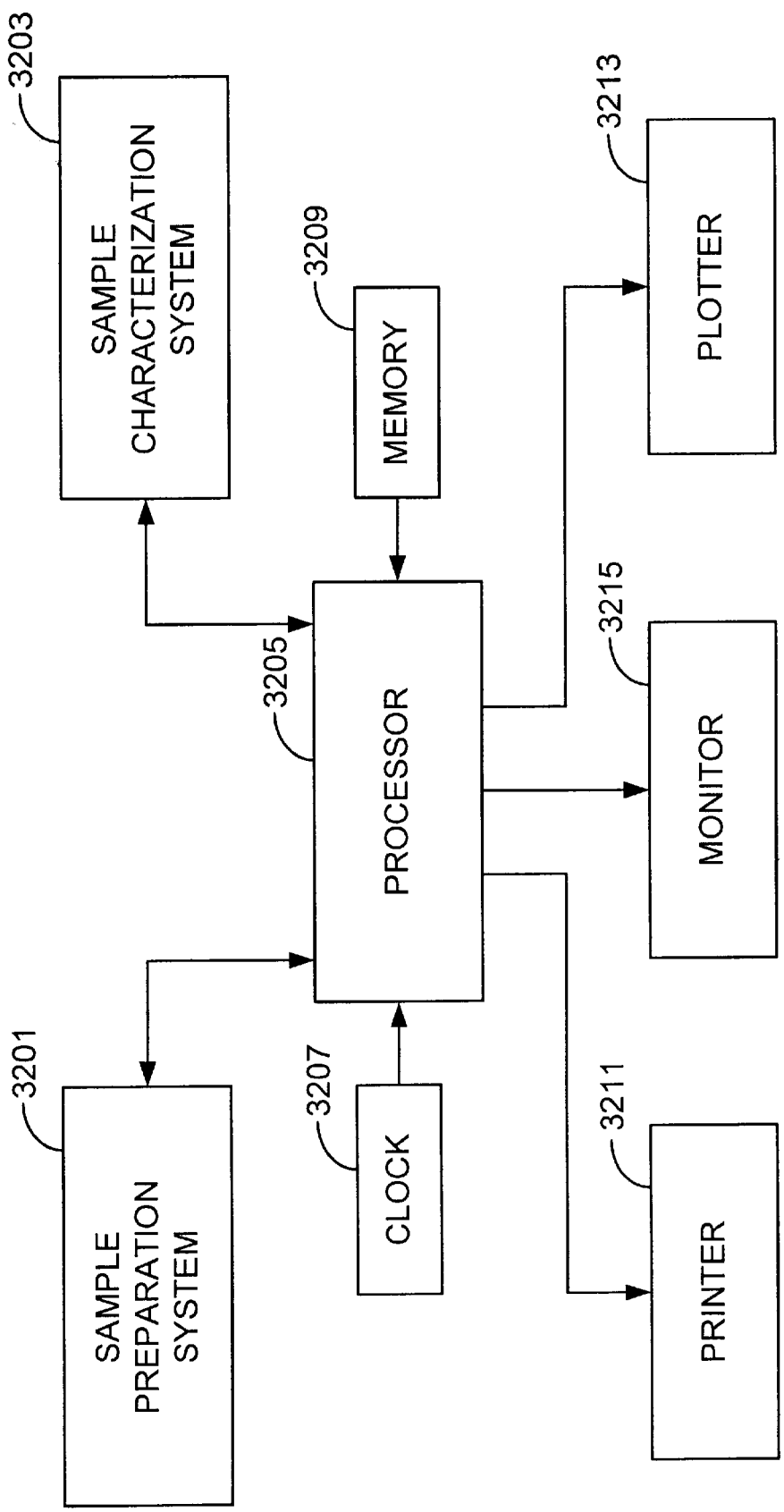
FIG. 32 is a schematic illustration of the principal components of a time tagging system according to at least one embodiment of the invention.
Figure 33:
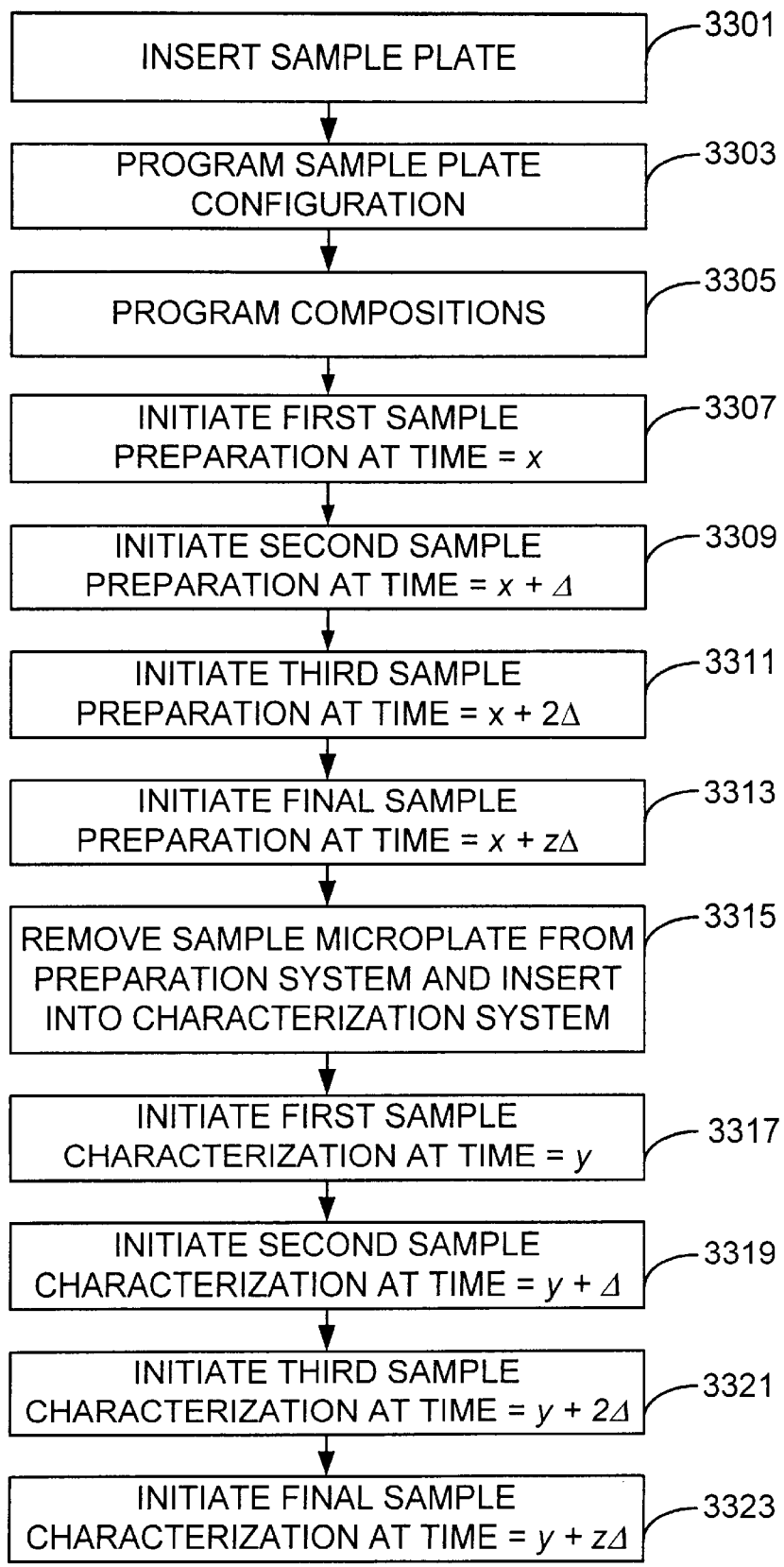
FIG. 33 illustrates the methodology associated with the embodiment shown in FIG. 32.

In a second time tagging mode illustrated in FIGS. 32 and 33, although a single time is used for an entire multi-assay plate, the discrepancies between samples are substantially eliminated. As shown, both a sample preparation system 3201 and a sample characterization system 3203 are controlled by a processor 3205. Although in the preferred embodiment a single processor 3205 is used to control both systems 3201 and 3203, multiple processors can be used as long as certain timing functions are programmable as described more fully below. Associated with processor 3205 is a clock 3207. Clock 3207 can be either an internal or an external clock. Although in the preferred embodiment clock 3207 provides an actual time (e.g., 2:32 PM), clock 3207 can also provide a running time. In the latter mode clock 3207 simply provides the amount of time that has passed between time tags. Also coupled to processor 3205 is a memory 3209, either internal or external to the processor, that records the time tags associated with each sample. Memory 3209 can be either volatile or non-volatile and utilize any of a variety of well known media (e.g., electronic, dynamic random access memory, magnetic media, capacitive and charge-storage systems, optical storage systems, etc.). Also attached to processor 3205 are one or more data presentation systems such as a printer 3211, a plotter 3213, and/or a monitor 3215.

Sample characterization system 3203 is a scanning fluorometer such as described above, preferably capable of measuring luminescence and absorption as well as fluorescence. Sample preparation system 3201 may be a robotically controlled, material preparation system such as is commonly known by those of skill in the art. In such a system a dispensing mechanism (e.g., micropipette, syringe, etc.) is typically attached to a 2- or 3-axis robotic stage. The dispensing system places the desired concentrations of each of the components into the individual sample wells of the multi-assay plate. The preparation system may also include means of mixing the components within the sample wells and means of varying the environment of the multi-assay plate (e.g., temperature, pressure, etc.). Sample preparation system 3201 can either be separate from, or combined with, characterization system 3205.

The methodology of this embodiment of the invention is illustrated in FIG. 33. Initially a sample plate is inserted into sample preparation system 3201 (step 3301) and processor 3205 is programmed with the type, size, and well configuration for the selected plate (step 3303). This programming provides the system with sufficient information to determine the locations of each of the sample wells within the plate. Alternatively, the system can utilize sensors or other means to locate the sample well positions. Processor 3205 is then programmed with the quantities of each of the individual components to be dispensed into the individual sample wells to create the desired compositions (step 3305).

Typically the initiation of each reaction within each sample well can be attributed to a single, controllable event such as the introduction of a reactant. If the reaction is initiated by the introduction of multiple reactants, often it is possible to simultaneously introduce the reactants, thus still resulting in a single reaction initiation time. Although the present example, illustrated in FIG. 33, assumes a single critical reaction initiation point, the present embodiment can also be used with more complicated, multi-critical event reactions. In this case, however, accurate time tagging is employed at each critical stage.

As illustrated in FIG. 33, the reaction within the first sample well of the multi-assay plate is initiated at a time equal to x (step 3307). Time x is recorded by processor 3205. The reaction within the second sample well is initiated at a second time equal to x+Δ (step 3309), where Δ is a known time interval. Similarly, the reaction within the third sample well is initiated at a third time equal to x+2Δ (step 3311). By spacing the reaction initiations at known, regular time intervals (step 3313), only the first time, x, must be recorded. After preparation of the sample multi-assay plate has been completed, the multi-assay plate is removed from sample preparation system 3201 and inserted into sample characterization system 3203, assuming that two different systems are employed (step 3315). The composition in the first sample well is then characterized at a time equal to y (step 3317), with time y being recorded by processor 3205. The second composition is characterized at a second time equal to y+Δ(step 3319), the third composition is characterized at a third time equal to y+2Δ (step 3321), and each subsequent composition is characterized using the same, known, regular time intervals (step 3323). Therefore assuming that the same order for sample preparation and sample characterization is used, this methodology requires that only two times be recorded, a sample preparation start time and a sample characterization start time, together with the time interval. This same methodology can be used with multiple characterization runs by simply recording the start time of each characterization run and maintaining the same order and time intervals.

In a specific example of this embodiment of the invention, a series of two primary component mixtures are first prepared in a multi-assay plate with 364 sample wells. A single reactant (i.e., a third component) is then added to each of the sample wells. The first sample well is prepared at 8:00 AM, with subsequent samples being prepared at 30 second time intervals thereafter. Thus the $121^{st}$ sample is prepared at 9:00 AM (i.e., 60 minutes for 120 samples, with a first sample at 8:00 AM). Using the present methodology, if the testing begins at 1:00 PM, the $121^{st}$ sample will be characterized at 2:00 PM. As a consequence, although only 2 times were recorded, 10:00 AM and 1:00 PM, all of the samples within the multi-assay plate can be directly compared since the time intervals between the preparation of individual samples and the time intervals between the characterization for individual samples is identical. Furthermore, the preparation time and/or the characterization time for any particular sample can be easily calculated using the known start time and the known time interval. Obviously much shorter time intervals may be employed for rapid analysis (e.g., 0.1 seconds or less).

In an alternative embodiment, sample preparation system 3201 and sample characterization system 3203 use two different processors. This embodiment offers the same benefits as the previous embodiments as long as the same time interval, Δ, is used by both processors and the initiation times for the two processors can be correlated.

The system illustrated in FIG. 32 can also be used in an alternative embodiment to apply a time tag to each individual sample. Preferably a time tag is applied at each critical sequence step for each sample within the multi-assay plate. For example, a time tag can be applied at each preparation step as well as during each characterization step. In addition, time tagging can be applied as external variables such as temperature, humidity, gas pressure, gas type, etc. are altered.

Figure 34:
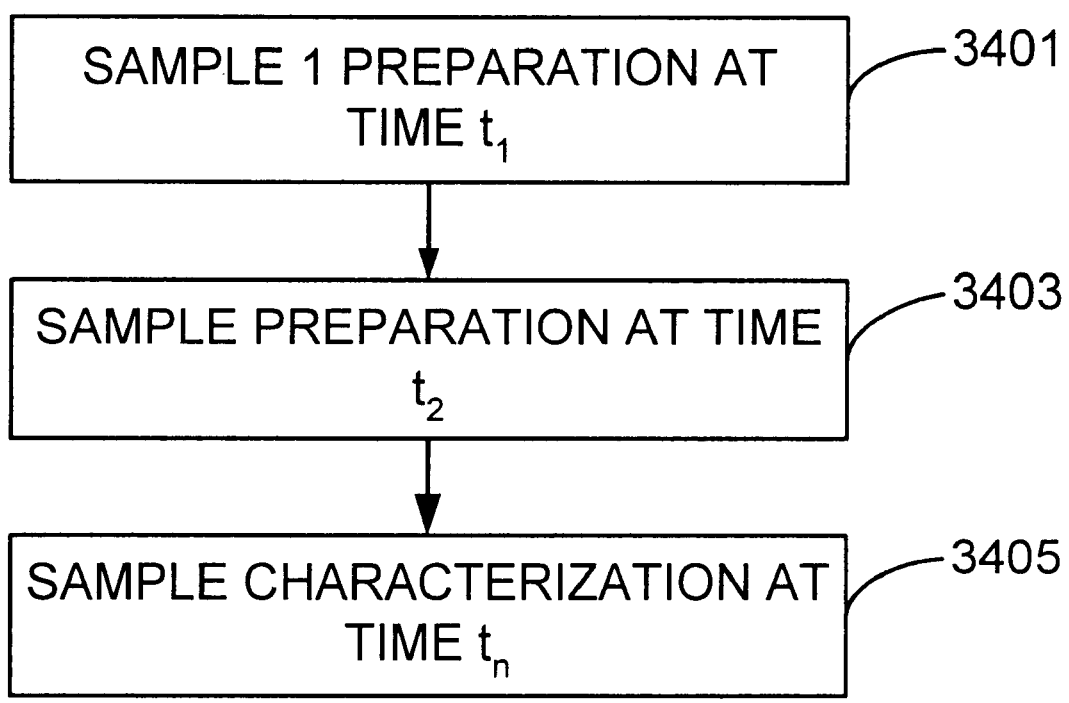
FIG. 34 illustrates the methodology associated with an alternative time tagging embodiment.

FIG. 34 illustrates the methodology of this embodiment of the invention. When the reaction of sample 1 is initiated, a time $t_1$, is recorded (step 3401). If necessary, multiple times can be recorded for the preparation of each sample, tagging each step or critical step of the process for each sample. For example, although it may only be necessary to tag the introduction of a reactant, it may be desirable to mark the introduction of each component of the composition, the starting and stopping times of a composition mixing process, etc. After sample 1 is tagged, a time $t_2$ is recorded for sample 2 (step 3403). This process continues until all of the samples to be prepared have been completed and tagged. The same process is then used to record a time tag, $t_n$, for each characterization run made for each sample (step 3405).

This embodiment provides greater flexibility than the previously described embodiment since it is not necessary to maintain a constant time interval between steps. Thus if some compositions are more complex than others in the series and thus take longer to prepare, the time interval can be varied to accommodate the differences in preparation time. Additionally, repetitive characterization runs can be made on select samples of the series instead of having to adhere to the same sequence throughout the test. For example, if the user is testing 100 different compositions, a preliminary characterization scan may show that 90 percent of the samples are not worth further consideration. The remaining 10 samples, however, can then be individually selected and a more thorough characterization performed on each of them. Once an experimental run is complete, the data can either be stored for later retrieval or immediately presented in a user-defined graphical or tabular format (e.g., absorption versus time; fluorescence versus composition versus time, etc.).

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A method of obtaining a wide dynamic range in a scanning fluorometer, the method comprising the steps of:

multiplexing an output from a photomultiplier tube detector in said scanning fluorometer through a plurality of gain amplifiers, each of said plurality of gain amplifiers providing a different level of gain, wherein said plurality of gain amplifiers includes a high gain amplifier providing the highest gain of said plurality of gain amplifiers;

determining a maximum photomultiplier tube detector supply voltage, wherein said maximum photomultiplier tube detector supply voltage provides an output signal from said high gain amplifier near a maximum value for a low reference; and determining at least one additional photomultiplier tube detector supply voltage, wherein said at least one additional photomultiplier tube detector supply voltage is lower than said maximum photomultiplier tube detector supply voltage.

2. The method of claim 1, wherein a first output range from said plurality of gain amplifiers when said photomultiplier tube detector supply voltage is set at said maximum supply voltage overlaps with a second output range from said plurality of gain amplifiers when said photomultiplier tube detector supply voltage is set at said at least one additional supply voltage.

3. The method of claim 1, further comprising a preamp/integrator, said preamp/integrator integrating said photomultiplier tube detector output.

4. The method of claim 1, wherein said step of determining a maximum photomultiplier tube detector supply voltage further comprises the steps of:

introducing said low reference into a measurement zone of said scanning fluorometer;

irradiating said low reference with light from an excitation source; and monitoring said photomultiplier tube detector output for said low reference.

5. The method of claim 4, wherein said low reference is a polystyrene sample.

6. The method of claim 1, wherein said plurality of gain amplifiers is comprised of four gain amplifiers.

7. A method of scanning a multi-well assay plate with a scanning fluorometer, the method comprising the steps of:

multiplexing an output from a photomultiplier tube detector in said scanning fluorometer through a plurality of gain amplifiers, each of said plurality of gain amplifiers providing a different level of gain, wherein said plurality of gain amplifiers includes a high gain amplifier providing the highest gain of said plurality of gain amplifiers;

determining a maximum photomultiplier tube detector supply voltage, wherein said maximum photomultiplier tube detector supply voltage provides an output signal from said high gain amplifier near a maximum value for a low reference;

determining at least one additional photomultiplier tube detector supply voltage, wherein said at least one additional photomultiplier tube detector supply voltage is lower than said maximum photomultiplier tube detector supply voltage, and wherein a first output range from said plurality of gain amplifiers when said photomultiplier tube detector supply voltage is set at said maximum supply voltage overlaps with a second output range from said plurality of gain amplifiers when said photomultiplier tube detector supply voltage is set at said at least one additional supply voltage;

scanning a plurality of wells of said multi-well assay plate with said scanning fluorometer a first time, wherein each scanned well of said multi-well assay plate is irradiated with light from an excitation source, wherein said photomultiplier tube detector supply voltage is set at said maximum photomultiplier tube detector supply voltage during said first scan;

monitoring said photomultiplier tube detector output for each scanned well of said multi-well assay plate;

optimizing said photomultiplier tube detector output with said plurality of gain amplifiers;

tagging wells of said plurality of wells of said multi-well assay plate when said photomultiplier tube detector output is outside of an acceptable range for all of said plurality of gain amplifiers;

at least scanning said tagged wells of said plurality of wells with said scanning fluorometer a second time, wherein each of said at tagged wells of said multi-well assay plate is irradiated with light from said excitation source, wherein said photomultiplier tube detector supply voltage is set at said at least one additional photomultiplier tube detector supply voltage during said second scan;

monitoring said photomultiplier tube detector output for at least said tagged wells of said plurality of wells; and optimizing said photomultiplier tube detector output with said plurality of gain amplifiers for at least said tagged wells of said plurality of wells.

8. The method of claim 7, said tagging step further comprising the step of recording a multi-well assay plate position for each of said tagged wells.

9. The method of claim 7, wherein during said step of scanning said plurality of wells of said multi-well assay plate each of said scanned wells is irradiated by multiple light flashes from said excitation source, and wherein during said step of at least scanning said tagged wells of said plurality of wells of said multi-well assay plate each of said tagged wells is irraditated by multiple light flashes from said excitation source.

10. The method of claim 9, further comprising the step of limiting said multiple light flashes to a single initial light flash if said photomultiplier tube detector output is outside of said acceptable range for all of said plurality of gain amplifiers for said single initial light flash.

11. The method of claim 7, wherein said step of at least scanning said tagged wells includes scanning untagged wells of said multi-well assay plate.

12. The method of claim 7, further comprising the step of processing said optimized photomultiplier tube detector output.

13. A method of scanning a multi-well assay plate with a scanning fluorometer, the method comprising the steps of:

selecting a photomultiplier tube detector supply voltage;

multiplexing an output from said photomultiplier tube detector in said scanning fluorometer through a plurality of gain amplifiers, each of said plurality of gain amplifiers providing a different level of gain;

scanning a plurality of wells of said multi-well assay plate with said scanning fluorometer, wherein each scanned well of said multi-well assay plate is irradiated with light from an excitation source;

monitoring said photomultiplier tube detector output for each scanned well of said multi-well assay plate;

optimizing said photomultiplier tube detector output with said plurality of gain amplifiers; and processing said optimized photomultiplier tube detector output.

14. A method of scanning a multi-well assay plate with a scanning fluorometer, the method comprising the steps of:
- multiplexing an output from a photomultiplier tube detector in said scanning fluorometer through a plurality of gain amplifiers, each of said plurality of gain amplifiers providing a different level of gain, wherein said plurality of gain amplifiers includes a high gain amplifier providing the highest gain of said plurality of gain amplifiers;
- determining a maximum photomultiplier tube detector supply voltage, wherein said maximum photomultiplier tube detector supply voltage provides an output signal from said high gain amplifier near a maximum value for a low reference;
- determining at least one additional photomultiplier tube detector supply voltage, wherein said at least one additional photomultiplier tube detector supply voltage is lower than said maximum photomultiplier tube detector supply voltage, and wherein a first output range from said plurality of gain amplifiers when said photomultiplier tube detector supply voltage is set at said maximum supply voltage overlaps with a second output range from said plurality of gain amplifiers when said photomultiplier tube detector supply voltage is set at said at least one additional supply voltage;
- scanning a plurality of wells of said multi-well assay plate with said scanning fluorometer a first time, wherein each scanned well of said multi-well assay plate is irradiated with a single flash of light from an excitation source, wherein said photomultiplier tube detector supply voltage is set at said at least one additional photomultiplier tube detector supply voltage during said first scan;
- monitoring said photomultiplier tube detector output for each scanned well of said multi-well assay plate;
- determining a preferred photomultiplier tube detector supply voltage for each scanned well of said multi-well assay plate;
- scanning said plurality of wells of said multi-well assay plate with said scanning fluorometer a second time, wherein each scanned well of said multi-well assay plate is irradiated with a predetermined number of flashes flash of light from said excitation source, wherein said photomultiplier tube detector supply voltage is set at said preferred photomultiplier tube detector supply voltage during said second scan; and
- monitoring said photomultiplier tube detector output for said plurality of wells for said second scan.

15. The method of claim 14, further comprising the step of optimizing said photomultiplier tube detector output with said plurality of gain amplifiers.

16. A wide dynamic range scanning fluorometer, comprising:
- a sample testing region;
- a source of excitation light coupled to said sample testing region;
- a photomultiplier tube detection system coupled to said sample testing region;
- a scanning mechanism, said scanning mechanism moving said excitation light source and said photomultiplier tube detection system relative to said sample testing region along at least one axis;
- a plurality of gain amplifiers coupled to said photomultiplier tube detection system, wherein each of said plurality of gain amplifiers provides a different level of gain, said plurality of gain amplifiers providing a range of gain;
- a photomultiplier tube power supply coupled to said photomultiplier tube, said power supply providing at least a first voltage and a second voltage to said photomultiplier tube, wherein a first gain range from said plurality of gain amplifiers when said power supply provides said first voltage overlaps a second gain range from said plurality of gain amplifiers when said power supply provides said second voltage; and
- a multiplexer coupled to said plurality of gain amplifiers, said multiplexer determining which of said plurality of gain amplifiers is coupled to a data processing system.

17. The wide dynamic range scanning fluorometer of claim 16, further comprising an analog to digital converter interposed between said multiplexer and said data processing system.

18. The wide dynamic range scanning fluorometer of claim 16, wherein said data processing system determines which of said at least said first voltage and said second voltage is provided to said photomultiplier tube.

19. The wide dynamic range scanning fluorometer of claim 16, further comprising a controller coupled to said photomultiplier tube power supply, said multiplexer, said scanning mechanism, said excitation source, and said photomultiplier tube detection system.

20. The wide dynamic range scanning fluorometer of claim 19, further comprising a rotatable grating and a plurality of filters interposed between said excitation source and said sample testing region, said rotatable grating and said plurality of filters controlling a wavelength corresponding to said excitation light, wherein said rotatable grating and said plurality of filters are coupled to said controller.

21. The wide dynamic range scanning fluorometer of claim 19, further comprising a rotatable grating and a plurality of filters interposed between said sample testing region and said photomultiplier tube detection system, said rotatable grating and said plurality of filters controlling an emission wavelength reaching said photomultiplier tube detection system, wherein said rotatable grating and said plurality of filters are coupled to said controller.

22. A method of optimizing a fluorometer prior to performing a sample scan, the method comprising the steps of:
- determining an expected emission peak;
- selecting a first emission system wavelength, wherein said first emission system wavelength is higher than said expected emission peak;
- scanning an excitation source from a first excitation source wavelength to a second excitation source wavelength, wherein both said first excitation source wavelength and said second excitation source wavelength are less than said first emission system wavelength;
- determining a peak excitation wavelength between said first excitation source wavelength and second excitation source wavelength;
- fixing said excitation source at a third excitation source wavelength, said third excitation source wavelength between said first excitation source wavelength and said second excitation source wavelength;
- scanning an emission system from a second emission system wavelength to a third emission system wavelength;
- determining a peak emission wavelength between said second emission system wavelength and said third emission system wavelength;

selecting a preferred emission filter;

fixing said preferred emission filter; and fixing said emission system at a fourth emission system wavelength.

23. The method of claim 22, wherein said first emission system wavelength is between about 20 and about 50 nanometers higher than said expected emission peak.

24. The method of claim 22, wherein said first emission system wavelength is about 35 nanometers higher than said expected emission peak.

25. The method of claim 22, wherein said second excitation source wavelength is about 20 nanometers less than said first emission system wavelength.

26. The method of claim 22, wherein said third excitation source wavelength is substantially equal to said peak excitation wavelength.

27. The method of claim 22, wherein said third excitation source wavelength is approximately 90 percent of said peak excitation wavelength.

28. The method of claim 22, further comprising the steps of:

sequentially inserting a plurality of emission filters into said fluorometer;

measuring a signal-to-background ratio for each emission filter of said plurality of emission filters; and determining said preferred emission filter from said plurality of emission filters, wherein said preferred emission filter has an optimal signal-to-background ratio.

29. The method of claim 22, wherein said fourth emission system wavelength is approximately 10 nanometers greater than a cutoff associated with said preferred emission filter.

* * * * *